US011917991B2

(12) United States Patent
Hassanein et al.

(10) Patent No.: US 11,917,991 B2
(45) Date of Patent: *Mar. 5, 2024

(54) SYSTEMS FOR MONITORING AND APPLYING ELECTRICAL CURRENTS IN AN ORGAN PERFUSION SYSTEM

(71) Applicant: TransMedics, Inc., Andover, MA (US)

(72) Inventors: Waleed H. Hassanein, North Andover, MA (US); Ahmed Elbetanony, North Andover, MA (US); Richard Bringham, North Andover, MA (US); Robert Havener, Lynnfield, MA (US); Vincent Lambert, II, Salisbury, MA (US); Burt Ochs, Andover, MA (US)

(73) Assignee: TRANSMEDICS, INC., Andover, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/418,250

(22) Filed: May 21, 2019

(65) Prior Publication Data

US 2019/0269125 A1    Sep. 5, 2019

Related U.S. Application Data

(60) Division of application No. 15/207,303, filed on Jul. 11, 2016, now Pat. No. 10,327,443, which is a
(Continued)

(51) Int. Cl.
*A01N 1/02* (2006.01)
*A61N 1/04* (2006.01)

(52) U.S. Cl.
CPC ......... *A01N 1/0247* (2013.01); *A01N 1/0294* (2013.01); *A61N 1/046* (2013.01); *A61N 1/0488* (2013.01); *A61N 1/0492* (2013.01)

(58) Field of Classification Search
CPC .... A01N 1/0247; A01N 1/0294; A61N 1/046; A61N 1/0488; A61N 1/0492
(Continued)

(56) References Cited

U.S. PATENT DOCUMENTS 3,253,595 A    5/1966    Keller, Jr. et al.
3,388,803 A    6/1968    Scott
(Continued)

FOREIGN PATENT DOCUMENTS

AU    2019236595 B2    12/2021
CA        2144952 A1     3/1994
(Continued)

OTHER PUBLICATIONS

US 11,758,904 B2, 09/2023, Freed (withdrawn)
(Continued)

*Primary Examiner* — Lydia Edwards
(74) *Attorney, Agent, or Firm* — Wilmer Cutler Pickering Hale and Dorr LLP

(57) ABSTRACT

Electrode systems have been developed for use in perfusion systems to measure the electrical activity of an explanted heart and to provide defibrillation energy as necessary. The perfusion systems maintain the heart in a beating state at, or near, normal physiological conditions; circulating oxygenated, nutrient enriched perfusion fluid to the heart at or near physiological temperature, pressure and flow rate. These systems include a pair of electrodes that are placed epicardially on the right atrium and left ventricle of the explanted heart, as well as an electrode placed in the aortic blood path.

22 Claims, 9 Drawing Sheets

Related U.S. Application Data continuation of application No. 11/822,495, filed on Jul. 6, 2007, now Pat. No. 9,457,179.

(60) Provisional application No. 60/919,306, filed on Mar. 20, 2007.

(58) Field of Classification Search
USPC ........................................................ 435/1.2
See application file for complete search history.

(56) References Cited

U.S. PATENT DOCUMENTS

| | | |
|---|---|---|
| 3,406,531 A | 10/1968 | Koski et al. |
| 3,468,136 A | 9/1969 | Koski et al. |
| 3,537,956 A | 11/1970 | Falcone |
| 3,545,221 A | 12/1970 | Koski et al. |
| 3,545,605 A | 12/1970 | Robins |
| 3,587,567 A | 6/1971 | Schiff |
| 3,607,646 A | 9/1971 | de Roissart |
| 3,632,473 A | 1/1972 | Belzer et al. |
| 3,639,084 A | 2/1972 | Goldhaber |
| 3,654,085 A | 4/1972 | Fritz et al. |
| 3,660,241 A | 5/1972 | Michielsen |
| 3,738,914 A | 6/1973 | Thorne et al. |
| 3,772,153 A | 11/1973 | De Roissart |
| 3,777,507 A | 12/1973 | Burton et al. |
| 3,843,455 A | 10/1974 | Bier et al. |
| 3,851,646 A | 12/1974 | Sams |
| 3,881,990 A | 5/1975 | Burton et al. |
| 3,995,444 A | 12/1976 | Clark et al. |
| 4,004,298 A | 1/1977 | Freed |
| 4,069,826 A | 1/1978 | Sessions |
| 4,186,253 A | 1/1980 | Yokoyama et al. |
| 4,186,565 A | 2/1980 | Toledo-Pereyra |
| 4,231,354 A | 11/1980 | Kurtz et al. |
| 4,415,556 A | 11/1983 | Bretschneider |
| 4,598,697 A | 7/1986 | Numazawa et al. |
| 4,605,644 A | 8/1986 | Foker |
| 4,666,425 A | 5/1987 | Fleming |
| 4,719,201 A | 1/1988 | Foker |
| 4,723,939 A | 2/1988 | Anaise |
| 4,745,759 A | 5/1988 | Bauer et al. |
| 4,759,371 A | 7/1988 | Franetzki |
| 4,801,299 A | 1/1989 | Brendel et al. |
| 4,847,470 A | 7/1989 | Bakke |
| 4,920,044 A | 4/1990 | Bretan, Jr. |
| 5,051,352 A | 9/1991 | Martindale et al. |
| 5,066,578 A | 11/1991 | Wikman-Coffelt |
| 5,141,847 A | 8/1992 | Sugimachi et al. |
| 5,145,771 A | 9/1992 | Lemasters et al. |
| 5,157,930 A | 10/1992 | McGhee et al. |
| 5,200,398 A | 4/1993 | Strasberg et al. |
| 5,217,860 A | 6/1993 | Fahy et al. |
| 5,285,657 A | 2/1994 | Bacchi et al. |
| 5,306,711 A | 4/1994 | Andrews |
| 5,326,706 A | 7/1994 | Yland et al. |
| 5,338,662 A | 8/1994 | Sadri |
| 5,354,268 A | 10/1994 | Peterson et al. |
| 5,356,593 A | 10/1994 | Heiberger et al. |
| 5,356,771 A | 10/1994 | O'Dell |
| 5,358,931 A | 10/1994 | Rubinsky et al. |
| 5,362,622 A | 11/1994 | O'Dell et al. |
| 5,370,989 A | 12/1994 | Stern et al. |
| 5,381,510 A | 1/1995 | Ford et al. |
| 5,385,821 A | 1/1995 | O'Dell et al. |
| 5,395,314 A | 3/1995 | Klatz et al. |
| 5,405,742 A | 4/1995 | Taylor |
| 5,407,669 A | 4/1995 | Lindstrom et al. |
| 5,407,793 A | 4/1995 | Del Nido et al. |
| 5,472,876 A | 12/1995 | Fahy |
| 5,473,791 A | 12/1995 | Holcomb et al. |
| 5,494,822 A | 2/1996 | Sadri |
| 5,498,427 A | 3/1996 | Menasche |
| 5,505,709 A | 4/1996 | Funderburk et al. |
| 5,514,536 A | 5/1996 | Taylor |
| 5,552,267 A | 9/1996 | Stern et al. |
| 5,554,123 A | 9/1996 | Herskowitz |
| 5,554,497 A | 9/1996 | Raymond |
| 5,571,801 A | 11/1996 | Segall et al. |
| 5,584,804 A | 12/1996 | Klatz et al. |
| 5,586,438 A | 12/1996 | Fahy |
| 5,588,816 A | 12/1996 | Abbott et al. |
| 5,599,173 A | 2/1997 | Chen et al. |
| 5,599,659 A | 2/1997 | Brasile et al. |
| 5,613,944 A | 3/1997 | Segall et al. |
| 5,643,712 A | 7/1997 | Brasile |
| 5,654,266 A | 8/1997 | Chen et al. |
| 5,656,420 A | 8/1997 | Chien |
| 5,679,565 A | 10/1997 | Mullen et al. |
| 5,693,462 A | 12/1997 | Raymond |
| 5,698,536 A | 12/1997 | Segall et al. |
| 5,699,793 A | 12/1997 | Brasile |
| 5,702,881 A | 12/1997 | Brasile et al. |
| 5,716,378 A | 2/1998 | Minten |
| 5,723,281 A | 3/1998 | Segall et al. |
| 5,733,894 A | 3/1998 | Segall et al. |
| 5,747,071 A | 5/1998 | Segall et al. |
| 5,752,929 A | 5/1998 | Klatz et al. |
| 5,759,148 A | 6/1998 | Sipin |
| 5,770,149 A | 6/1998 | Raible |
| 5,776,063 A | 7/1998 | Dittrich et al. |
| 5,786,136 A | 7/1998 | Mayer |
| 5,787,544 A | 8/1998 | Meade |
| 5,807,737 A | 9/1998 | Schill et al. |
| 5,823,799 A | 10/1998 | Tor et al. |
| 5,843,024 A | 12/1998 | Brasile |
| 5,856,081 A | 1/1999 | Fahy |
| 5,882,328 A | 3/1999 | Levy et al. |
| 5,965,433 A | 10/1999 | Gardetto et al. |
| 5,998,240 A | 12/1999 | Hamilton et al. |
| 6,024,698 A | 2/2000 | Brasile |
| 6,034,109 A | 3/2000 | Ramasamy et al. |
| 6,042,550 A | 3/2000 | Haryadi et al. |
| 6,046,046 A | 4/2000 | Hassanein |
| 6,050,987 A | 4/2000 | Rosenbaum |
| 6,090,776 A | 7/2000 | Kuberasampath et al. |
| 6,100,082 A | 8/2000 | Hassanein |
| 6,110,139 A | 8/2000 | Loubser |
| 6,110,504 A | 8/2000 | Segall et al. |
| 6,144,444 A | 11/2000 | Haworth et al. |
| 6,168,877 B1 | 1/2001 | Pedicini et al. |
| 6,217,546 B1 | 4/2001 | Hinchliffe et al. |
| 6,365,338 B1 | 4/2002 | Bull et al. |
| 6,375,611 B1 | 4/2002 | Voss et al. |
| 6,375,613 B1 | 4/2002 | Brasile |
| 6,389,308 B1 | 5/2002 | Shusterman |
| 6,402,461 B1 | 6/2002 | Tebby |
| 6,475,716 B1 | 11/2002 | Seki |
| 6,490,880 B1 | 12/2002 | Walsh |
| 6,492,103 B1 | 12/2002 | Taylor |
| 6,492,745 B1 | 12/2002 | Colley, III et al. |
| 6,524,785 B1 | 2/2003 | Cozzone et al. |
| 6,526,974 B1 | 3/2003 | Brydon et al. |
| 6,569,615 B1 | 5/2003 | Thatte et al. |
| 6,582,375 B2 | 6/2003 | Melvin et al. |
| 6,582,953 B2 | 6/2003 | Brasile |
| 6,600,941 B1 | 7/2003 | Khuri |
| 6,609,987 B1 | 8/2003 | Beardmore |
| 6,631,830 B2 | 10/2003 | Ma et al. |
| 6,642,045 B1 | 11/2003 | Brasile |
| 6,673,594 B1 | 1/2004 | Owen et al. |
| 6,696,238 B2 | 2/2004 | Murphy et al. |
| 6,740,484 B1 | 5/2004 | Khirabadi et al. |
| 6,764,462 B2 | 7/2004 | Risk, Jr. et al. |
| 6,783,328 B2 | 8/2004 | Lucke et al. |
| 6,792,309 B1 | 9/2004 | Noren |
| 6,794,124 B2 | 9/2004 | Steen |
| 6,811,965 B2 | 11/2004 | Vodovotz et al. |
| 6,837,851 B1 | 1/2005 | Coroneo |
| 6,878,339 B2 | 4/2005 | Akiyama et al. |
| 6,894,690 B2 | 5/2005 | Capers |
| 6,906,325 B2 | 6/2005 | Quek |
| 6,925,324 B2 | 8/2005 | Shusterman |
| 6,953,655 B1 | 10/2005 | Hassanein et al. |

(56) References Cited

U.S. PATENT DOCUMENTS

| | | |
|---|---|---|
| 6,974,436 B1 | 12/2005 | Aboul-Hosn et al. |
| 7,001,354 B2 | 2/2006 | Suzuki et al. |
| 7,008,380 B1 | 3/2006 | Rees et al. |
| 7,045,279 B1 | 5/2006 | Laske et al. |
| 7,238,165 B2 | 7/2007 | Vincent et al. |
| 7,316,666 B1 | 1/2008 | Entenman et al. |
| 7,410,474 B1 | 8/2008 | Friend et al. |
| 7,431,727 B2 | 10/2008 | Cole et al. |
| 7,452,711 B2 | 11/2008 | Daykin |
| 7,572,622 B2 | 8/2009 | Hassanein et al. |
| 7,651,835 B2 | 1/2010 | Hassanein et al. |
| 7,811,808 B2 | 10/2010 | Van Der Plaats et al. |
| 8,167,869 B2 | 5/2012 | Wudyka |
| 8,304,181 B2 | 11/2012 | Hassanein et al. |
| 8,323,954 B2 | 12/2012 | Kravitz et al. |
| 8,409,846 B2 | 4/2013 | Hassanein et al. |
| 8,420,380 B2 | 4/2013 | Fishman et al. |
| 8,465,970 B2 | 6/2013 | Hassanein et al. |
| 8,535,934 B2 | 9/2013 | Hassanein et al. |
| 8,585,380 B2 | 11/2013 | Hassanein et al. |
| 8,715,305 B2 | 5/2014 | Pate et al. |
| 8,822,203 B2 | 9/2014 | Hassanein et al. |
| 9,055,740 B2 | 6/2015 | Hassanein et al. |
| 9,215,867 B2 | 12/2015 | Hassanein et al. |
| 9,457,179 B2 | 10/2016 | Hassanein et al. |
| 9,462,802 B2 | 10/2016 | Fishman et al. |
| 9,706,768 B2 | 7/2017 | Freed et al. |
| 9,894,894 B2 | 2/2018 | Hassanein et al. |
| 10,076,112 B2 | 9/2018 | Hassanein et al. |
| 10,124,093 B1 | 11/2018 | Francis et al. |
| 10,321,676 B2 | 6/2019 | Hassanein et al. |
| 10,327,441 B2 | 6/2019 | Freed et al. |
| 10,362,780 B2 | 7/2019 | Kay et al. |
| 10,433,539 B2 | 10/2019 | White et al. |
| 10,736,314 B2 | 8/2020 | Hassanein et al. |
| 10,750,738 B2 | 8/2020 | Fishman et al. |
| 11,122,795 B2 | 9/2021 | Hassanian et al. |
| 11,154,050 B2 | 10/2021 | Hassanein et al. |
| 11,191,263 B2 | 12/2021 | Hassanein et al. |
| 11,570,985 B2 | 2/2023 | Hassanein et al. |
| 11,723,357 B2 | 8/2023 | Hassanein et al. |
| 2001/0003652 A1 | 6/2001 | Freeman |
| 2001/0018569 A1 | 8/2001 | Erbel et al. |
| 2001/0025191 A1 | 9/2001 | Montgomery |
| 2002/0012988 A1 | 1/2002 | Brasile |
| 2002/0102720 A1 | 8/2002 | Steen |
| 2002/0132220 A1 | 9/2002 | Berens et al. |
| 2002/0151950 A1 | 10/2002 | Okuzumi |
| 2002/0164795 A1 | 11/2002 | Gen |
| 2002/0177117 A1 | 11/2002 | Wolf |
| 2002/0187132 A1 | 12/2002 | Mcgregor et al. |
| 2002/0198504 A1 | 12/2002 | Risk et al. |
| 2003/0040665 A1 | 2/2003 | Khuri et al. |
| 2003/0050689 A1 | 3/2003 | Matson |
| 2003/0053998 A1 | 3/2003 | Daemen et al. |
| 2003/0073227 A1 | 4/2003 | Hull et al. |
| 2003/0073912 A1 | 4/2003 | Melvin et al. |
| 2003/0074760 A1 | 4/2003 | Keller |
| 2003/0086830 A1 | 5/2003 | Haywood et al. |
| 2003/0111604 A1 | 6/2003 | Quek |
| 2003/0124503 A1 | 7/2003 | Olivencia-Yurvati et al. |
| 2003/0135152 A1 | 7/2003 | Kollar et al. |
| 2003/0147466 A1 | 8/2003 | Liang |
| 2003/0168064 A1 | 9/2003 | Daly et al. |
| 2004/0015042 A1 | 1/2004 | Vincent et al. |
| 2004/0017658 A1 | 1/2004 | Lo et al. |
| 2004/0018966 A1 | 1/2004 | Segall et al. |
| 2004/0029096 A1 | 2/2004 | Steen |
| 2004/0038192 A1 | 2/2004 | Brasile |
| 2004/0058432 A1 | 3/2004 | Owen et al. |
| 2004/0082057 A1 | 4/2004 | Alford et al. |
| 2004/0086578 A1 | 5/2004 | Segall et al. |
| 2004/0102415 A1 | 5/2004 | Thatte et al. |
| 2004/0102678 A1 | 5/2004 | Haindl |
| 2004/0106958 A1 | 6/2004 | Mathis et al. |
| 2004/0110800 A1 | 6/2004 | Bril et al. |
| 2004/0115689 A1 | 6/2004 | Augello et al. |
| 2004/0138542 A1 | 7/2004 | Khuri et al. |
| 2004/0168341 A1 | 9/2004 | Petersen et al. |
| 2004/0170950 A1 | 9/2004 | Prien |
| 2004/0171138 A1 | 9/2004 | Hassanein et al. |
| 2004/0193096 A1 | 9/2004 | Cooper |
| 2004/0202993 A1 | 10/2004 | Poo et al. |
| 2004/0221719 A1 | 11/2004 | Wright et al. |
| 2004/0224298 A1 | 11/2004 | Brassil et al. |
| 2004/0235142 A1 | 11/2004 | Schein et al. |
| 2004/0236170 A1 | 11/2004 | Kim |
| 2004/0248281 A1 | 12/2004 | Wright et al. |
| 2004/0258745 A1 | 12/2004 | Kai et al. |
| 2005/0010118 A1 | 1/2005 | Toyoda et al. |
| 2005/0019917 A1 | 1/2005 | Toledo-Pereyra et al. |
| 2005/0027237 A1 | 2/2005 | Weiner |
| 2005/0037330 A1 | 2/2005 | Fischer et al. |
| 2005/0063860 A1 | 3/2005 | Carpenter et al. |
| 2005/0085762 A1 | 4/2005 | Vijay et al. |
| 2005/0142532 A1 | 6/2005 | Poo et al. |
| 2005/0147958 A1 | 7/2005 | Hassanein et al. |
| 2005/0153271 A1 | 7/2005 | Wenrich |
| 2005/0170019 A1 | 8/2005 | Roth |
| 2005/0182349 A1 | 8/2005 | Linde et al. |
| 2005/0187469 A1 | 8/2005 | Phillips |
| 2005/0202394 A1 | 9/2005 | Dobson |
| 2005/0253390 A1 | 11/2005 | Blazek |
| 2005/0255442 A1 | 11/2005 | Brassil et al. |
| 2006/0034941 A1 | 2/2006 | Dobson |
| 2006/0039870 A1 | 2/2006 | Turner |
| 2006/0074470 A1 | 4/2006 | Bartels et al. |
| 2006/0121438 A1 | 6/2006 | Toledo-Pereyra et al. |
| 2006/0124130 A1 | 6/2006 | Bonassa |
| 2006/0134073 A1 | 6/2006 | Naka et al. |
| 2006/0148062 A1 | 7/2006 | Hassanein et al. |
| 2006/0154357 A1 | 7/2006 | Hassanein et al. |
| 2006/0154358 A1 | 7/2006 | Hassanein et al. |
| 2006/0154359 A1 | 7/2006 | Hassanein et al. |
| 2006/0160204 A1 | 7/2006 | Hassanein et al. |
| 2006/0166360 A1 | 7/2006 | Berthiaume et al. |
| 2006/0182722 A1 | 8/2006 | Hering et al. |
| 2006/0292544 A1 | 12/2006 | Hassanein et al. |
| 2007/0009881 A1 | 1/2007 | Arzt et al. |
| 2007/0098694 A1 | 5/2007 | Khuri et al. |
| 2007/0135752 A1 | 6/2007 | Domash et al. |
| 2007/0135760 A1 | 6/2007 | Williams |
| 2007/0196461 A1 | 8/2007 | Weers |
| 2007/0275364 A1 | 11/2007 | Hassanein et al. |
| 2008/0009815 A1 | 1/2008 | Grabenkort et al. |
| 2008/0017191 A1 | 1/2008 | Davies et al. |
| 2008/0017194 A1 | 1/2008 | Hassanein et al. |
| 2008/0057488 A1 | 3/2008 | Steen |
| 2008/0234768 A1 | 9/2008 | Hassanein et al. |
| 2008/0286746 A1 | 11/2008 | Poo et al. |
| 2008/0295839 A1 | 12/2008 | Habashi |
| 2009/0142830 A1 | 6/2009 | Yamashiro et al. |
| 2009/0143417 A1 | 6/2009 | Smith et al. |
| 2009/0182302 A1 | 7/2009 | Garabet |
| 2009/0191614 A1 | 7/2009 | Miyahara |
| 2009/0197240 A1 | 8/2009 | Fishman et al. |
| 2009/0197241 A1 | 8/2009 | Fishman et al. |
| 2009/0197292 A1 | 8/2009 | Fishman et al. |
| 2009/0197324 A1 | 8/2009 | Fishman et al. |
| 2009/0197325 A1 | 8/2009 | Fishman et al. |
| 2009/0215022 A1 | 8/2009 | Page et al. |
| 2009/0312724 A1 | 12/2009 | Pipkin et al. |
| 2010/0028850 A1 | 2/2010 | Brasill |
| 2010/0056966 A1 | 3/2010 | Toth |
| 2010/0092939 A1 | 4/2010 | Belous et al. |
| 2010/0119554 A1 | 5/2010 | Dobson |
| 2010/0204663 A1 | 8/2010 | Wudyka |
| 2010/0322826 A1 | 12/2010 | Locascio et al. |
| 2010/0322862 A1 | 12/2010 | Ruoslahti et al. |
| 2011/0002926 A1 | 1/2011 | Matthews et al. |
| 2011/0076666 A1 | 3/2011 | Brasill |
| 2011/0129810 A1 | 6/2011 | Owen et al. |
| 2011/0136096 A1 | 6/2011 | Hassanein et al. |
| 2011/0177487 A1 | 7/2011 | Simsir et al. |

(56) References Cited

U.S. PATENT DOCUMENTS

| | | |
|---|---|---|
| 2011/0190572 A1 | 8/2011 | Brophy et al. |
| 2011/0212431 A1 | 9/2011 | Bunegin et al. |
| 2011/0294108 A1 | 12/2011 | Argoudelis et al. |
| 2012/0064050 A1 | 3/2012 | Calle et al. |
| 2012/0077771 A1 | 3/2012 | Fallouh et al. |
| 2012/0183945 A1 | 7/2012 | Steen et al. |
| 2012/0277681 A1 | 11/2012 | Kravitz et al. |
| 2012/0282591 A1 | 11/2012 | Thatte et al. |
| 2012/0330438 A1 | 12/2012 | Keshavjee et al. |
| 2013/0011823 A1 | 1/2013 | Hassanein et al. |
| 2013/0078710 A1 | 3/2013 | Hassanein et al. |
| 2013/0102917 A1 | 4/2013 | Colbaugh et al. |
| 2013/0144227 A1 | 6/2013 | Locke et al. |
| 2013/0157248 A1 | 6/2013 | Fishman et al. |
| 2013/0220325 A1 | 8/2013 | Davis et al. |
| 2013/0295552 A1 | 11/2013 | Hassanein et al. |
| 2014/0001745 A1 | 1/2014 | Lehmann et al. |
| 2014/0007961 A1 | 1/2014 | Steen et al. |
| 2014/0017658 A1 | 1/2014 | Steinman et al. |
| 2014/0017660 A1 | 1/2014 | Steinman et al. |
| 2014/0135738 A1 | 5/2014 | Panian |
| 2014/0220550 A1 | 8/2014 | Van Der Plaats et al. |
| 2014/0283828 A1 | 9/2014 | Acker et al. |
| 2014/0308654 A1 | 10/2014 | Kay et al. |
| 2014/0377849 A1 | 12/2014 | Kay et al. |
| 2015/0017710 A1 | 1/2015 | Freed et al. |
| 2015/0079580 A1 | 3/2015 | Hassanein et al. |
| 2015/0093738 A1 | 4/2015 | Potenziano et al. |
| 2015/0230453 A1 | 8/2015 | Fontes et al. |
| 2015/0246164 A1 | 9/2015 | Heaton et al. |
| 2015/0275176 A1 | 10/2015 | Kobayashi et al. |
| 2015/0342177 A1 | 12/2015 | Hassanein et al. |
| 2016/0113269 A1 | 4/2016 | Woodard et al. |
| 2016/0262634 A1 | 9/2016 | Steen et al. |
| 2016/0361476 A1 | 12/2016 | Huang |
| 2017/0000110 A1 | 1/2017 | Korkut et al. |
| 2017/0015963 A1 | 1/2017 | Ott |
| 2017/0042141 A1 | 2/2017 | Kay et al. |
| 2017/0049096 A1 | 2/2017 | Kay et al. |
| 2019/0021308 A1 | 1/2019 | Hassanein et al. |
| 2020/0128813 A1 | 4/2020 | Kay et al. |
| 2020/0337298 A1 | 10/2020 | Hassanein et al. |
| 2020/0352155 A1 | 11/2020 | Fishman et al. |
| 2021/0244017 A1 | 8/2021 | Ritchie et al. |
| 2022/0039373 A1 | 2/2022 | Hassanein et al. |
| 2022/0071197 A1 | 3/2022 | Hassanein et al. |
| 2022/0232823 A1 | 7/2022 | Hassanein et al. |
| 2022/0361482 A1 | 11/2022 | Hassanein |
| 2023/0210104 A1 | 7/2023 | Hassanein |
| 2023/0263156 A1 | 8/2023 | Hassanein |

FOREIGN PATENT DOCUMENTS

| | | |
|---|---|---|
| CA | 2881613 A1 | 11/2007 |
| CA | 2861545 A1 | 7/2013 |
| CA | 2521324 C | 12/2014 |
| CA | 2985229 | 2/2023 |
| CN | 1232723 A | 10/1999 |
| CN | 1269471 A | 10/2000 |
| CN | 2418882 Y | 2/2001 |
| CN | 1452863 A | 11/2003 |
| CN | 2616058 Y | 5/2004 |
| CN | 1849102 A | 10/2006 |
| CN | 101072500 A | 11/2007 |
| CN | 101404968 A | 4/2009 |
| CN | 101977649 A | 2/2011 |
| CN | 103596426 A | 2/2014 |
| CN | 103893205 A | 7/2014 |
| CN | 203724222 U | 7/2014 |
| CN | 104770361 A | 7/2015 |
| DE | 4201259 A1 | 7/1993 |
| DE | 10121159 A1 | 11/2002 |
| DE | 102005048625 A1 | 4/2007 |
| EP | 0347923 | 12/1989 |
| EP | 0376763 | 7/1990 |
| EP | 1017271 B1 | 7/2000 |
| EP | 1062870 B1 | 1/2003 |
| EP | 1488743 A2 | 12/2004 |
| EP | 1942726 A2 | 7/2008 |
| EP | 3347084 | 11/2020 |
| EP | 4032401 A1 | 7/2022 |
| FR | 2830183 A1 | 4/2003 |
| JP | S57-010695U1 A | 1/1982 |
| JP | 63270601 A | 11/1988 |
| JP | H02-282301 A | 11/1990 |
| JP | 02-306901 A | 12/1990 |
| JP | H03-74302 A | 3/1991 |
| JP | 04-099701 A | 3/1992 |
| JP | H04-128201 A | 4/1992 |
| JP | 06-056601 | 3/1994 |
| JP | 06-305901 | 11/1994 |
| JP | H07-196401 A | 8/1995 |
| JP | H08-89518 A | 4/1996 |
| JP | 08-511012 | 11/1996 |
| JP | H09-500481 A | 1/1997 |
| JP | 2001061956 A | 3/2001 |
| JP | 2001516768 A | 10/2001 |
| JP | 2002-119586 A | 4/2002 |
| JP | 2003-206201 A | 7/2003 |
| JP | 2003-315220 A | 11/2003 |
| JP | 2004513889 A | 5/2004 |
| JP | 2004525290 A | 8/2004 |
| JP | 2004529938 A | 9/2004 |
| JP | 2008-515914 A | 5/2008 |
| JP | 2009-521931 A | 6/2009 |
| JP | 2010-525076 A | 7/2010 |
| JP | 2011-511000 A | 4/2011 |
| JP | 2016-053030 | 4/2016 |
| JP | 6144238 B2 | 6/2017 |
| JP | 6625384 B2 | 12/2019 |
| JP | 6756775 B2 | 9/2020 |
| JP | 6757829 B2 | 9/2020 |
| WO | WO-8805261 | 7/1988 |
| WO | WO-9502326 A1 | 1/1995 |
| WO | WO-95/03680 A1 | 2/1995 |
| WO | WO-9531897 | 11/1995 |
| WO | WO-9618293 | 6/1996 |
| WO | WO-9629865 | 10/1996 |
| WO | WO-9722244 A1 | 6/1997 |
| WO | WO-9746091 | 12/1997 |
| WO | WO-9915011 A1 | 4/1999 |
| WO | WO-00/18226 | 4/2000 |
| WO | WO-0022927 A1 | 4/2000 |
| WO | WO-200027189 A1 | 5/2000 |
| WO | WO-00/35340 A1 | 6/2000 |
| WO | WO-0060936 A1 | 10/2000 |
| WO | WO-200101774 A1 | 1/2001 |
| WO | WO-0226034 A2 | 4/2002 |
| WO | WO-02/35929 A1 | 5/2002 |
| WO | WO-02089571 A1 | 11/2002 |
| WO | WO-2003026419 A1 | 4/2003 |
| WO | WO-2004017838 | 3/2004 |
| WO | WO-2004026031 A2 | 4/2004 |
| WO | WO-2006042138 A2 | 4/2006 |
| WO | WO-2006060309 | 6/2006 |
| WO | WO-2006076590 A2 | 7/2006 |
| WO | WO-2006124820 A2 | 11/2006 |
| WO | WO-2007079185 A2 | 7/2007 |
| WO | WO-2007124044 A2 | 11/2007 |
| WO | WO-2008106724 A1 | 9/2008 |
| WO | WO-2008108996 A1 | 9/2008 |
| WO | WO-08150587 A2 | 12/2008 |
| WO | WO-2009/099939 A2 | 8/2009 |
| WO | WO-2011002926 A2 | 1/2011 |
| WO | WO-2011072012 A2 | 6/2011 |
| WO | WO-2012142487 A1 | 10/2012 |
| WO | WO-2012/148685 | 11/2012 |
| WO | WO-2013068751 | 5/2013 |
| WO | WO-2013068752 A2 | 5/2013 |
| WO | WO-2013068753 | 5/2013 |
| WO | WO-2013106908 A1 | 7/2013 |
| WO | WO-2014011547 A2 | 1/2014 |
| WO | WO-2014059316 A1 | 4/2014 |
| WO | WO-2014194349 A1 | 12/2014 |

(56) References Cited

FOREIGN PATENT DOCUMENTS

| | | |
|---|---|---|
| WO | WO-2015126853 A1 | 8/2015 |
| WO | WO-2015143552 A1 | 10/2015 |
| WO | WO-2015154170 A1 | 10/2015 |
| WO | WO-2015154193 A1 | 10/2015 |
| WO | WO-2015187737 | 12/2015 |
| WO | WO-2016090498 A1 | 6/2016 |
| WO | WO-2017044465 | 3/2017 |
| WO | WO-2017205967 A1 | 12/2017 |

OTHER PUBLICATIONS

Extended European Search Report Issued In European Patent Application No. 19204566.4, dated May 25, 2020 (7 pages).
Gever, J., "Technique to Repair Damaged Donor Lungs for Graft Passes Clinical Test", MedPage Today, https://www.medpagetoday.org/surgery/transplantation/12245, Accessed Jul. 11, 2020, dated Dec. 19, 2008 (4 pages).
Hai, Human Body Atlas, First Edition, Liaoning Science and Technology Publishing House, p. 120, Oct. 31, 2011 (3 pages)—with English Translation.
Keshavjee, S.H. et al., "The role of dextran 40 and potassium in extended hypothermic lung preservation for transplantation", Journal of Thoracic and Cardiovascular Surgery, 103(2):314-325, Feb. 1992 (12 pages).
Wei, Y. et al., "Protective Effect of Specific Phosphodiesterase Inhibitor Milrinone for Donor Lungs", Chinese Journal of New Drugs, 16(21):1762-1765, 2007—English Translation issued by U.S. Patent and Trademark Office, Aug. 2020 (17 pages).
"2002 Design & Engineering Awards, Portable Organ Preservation System", Science (2002) (1 page).
"Celsior™ Cold Storage Solution", Sangstat Medical Corporation (internet reference) (1999) (5 pages).
"History of Transplantation and Organ Preservation," Barr Laboratories, Inc. (2004) (4 pages).
"Human heart beats on its own outside body", USA Today (2001) (1 page).
"Human Heart Kept Alive Outside Body for First Time in Study of Portable Organ Preservation System™ at University of Pittsburgh Medical Center", UPMC, McGowan Institute for Regenerative Medicine (2001) (2 pages).
"Machine Keeps Human Kidney Alive for24-Hours", American Academy of Anti-Aging Medicine, 222.worldhealth.net, Aug. 25, 2001, (<http://wwwworldhealth.net/p/393,1313.htm>) by Richard Klatz , Accessed Jul. 5, 2006 (1 page).
"Machine May Be Organ Transplant Breakthrough," USA Today (Aug. 2001), 1 page.
"New discovery in organ transplantation", MSNBC Chicago, No Author Listed (2001) (www.nbc5/com <http://www.nbc5/com>) (1 page).
"The Nation: Warm-Storage Device May Aid Organ Transplants", Dow Jones Publications Library (2001) (1 page).
"ViaSpan (Belzer UW) Cold Storage Solution", Barr Laboratories, Inc. (2002), 2 pages.
"Warm storage for donor organs", University of Chicago Magazine (2001) (1 page).
Ahmad, N. et al., "A pathophysiologic study of the kidney tubule to optimize organ preservation solutions", Kidney International 66(1):77-90 (2004), 14 pages.
Aitchison, J. Douglas et al. "Nitric Oxide During Perfusion Improves Posttransplantation Function of Non-Heart-Beating Donor Lungs." Transplantation. Jun. 27, 2003. vol. 75, No. 12, pp. 1960-1964.
Aitchison, J.D. et al., "Functional assessment of non-heart-beating donor lungs: prediction of post-transplant function", European Journal of Cardio-thoracic Surgery, 20:187-194 (2001) (8 pages).
Anathaswamy, A., "Machine keeps organs alive for longer", NewScientist.com, Aug. 16, 2001, (<http://www.newscientist.com/article.ns?id=dn1168&print=true> (1 page).

Aoki, M. et al., Anti-CD18 Attenuates Deleterious Effects of Cardiopulmonary Bypass and Hypothermic Circulatory Arrest in Piglets, J. Card. Surg. 10(Suppl):407-17 (1995) (11 pages).
Bando, K. et al., "Oxygenated perfluorocarbon, recombinant human superoxide dismutase, and catalase ameliorate free radical induced myocardial injury during heart preservation and transplantation", J. Thorac Cardiovasc Surg. 96:930-8 (Dec. 1988), 9 pages.
Barinov, E.F., "Hormonal-metabolic disturbances during biological preservation of the heart", Fiziologicheskii Zhurnal (Kiev), 29(3):293-299 (1983) (8 pages)—Russian Language with English Abstract.
Belzer, F.O., "Formula for Belzer MPS Solution", University of Wisconsin-Madison Organ Preservation, (<http://www.surgery.wisc.edu/transplat/research/southard/BelzerMPS.shtml>) (Oct. 3, 2003) (2 pages).
Benichou, J. et al., "Canine and Human Liver Preservation for 6 to 18 HR by Cold Infusion", Transplantation, 24(6):407-411 (Dec. 1977) (5 pages).
Birkett, D. et al., "The Fatty Acid Content and Drug Binding Characteristics of Commercial Albumin Preparations", Clinica Chimica Acta 85:253-258 (1978), 6 pages.
Blanchard, J.M. et al., "Techniques for Perfusion and Storage of Heterotopic Heart Transplants in Mice", Microsurgery, 6:169-174 (1985), 6 pages.
Boggi, U. et al., "Pancreas Preservation with University of Wisconsin and Celsior Solutions", Transplant Proceedings 36(3):563-565 (2004), 3 pages.
Boggi, U. et al., "Pancreas Preservation With University of Wisconsin and Celsior Solutions: A Single-Center, Prospective, Randomized Pilot Study", Transplantation 27:77(8):1186-1190 (2004), 5 pages.
Botha, P., "Extended Donor Criteria in Lung Transplantation", Current Opinion in Organ Transplantation, 14:206-210, 2009 (5 pages).
Boyle, E.M. Jr. et al., "Ischemia-Reperfusion Injury", Ann. Thorac. Surg. 64:S24-S30 (1997), 7 pages.
Brandes, H. et al. "Influence of High Molecular Dextrans on Lung Function in an ex Vivo Porcine Lung Model," Journal of Surgical Research, 101:2, 225-231 (2001) (7 pages).
Brasile, L. et al. "Organ Preservation Without Extreme Hypothermia Using an Oxygent™ Supplemented Perfusate", Art. Cells, Blood Subs., and Immob. Biotech., 22(4):1463-68 (1994), 6 pages.
Burt, J.M. et al., "Myocardial function after preservation for 24 hours", J. Thorac. Cardiovasc Surg., 92(2):238-46 (1986), 9 pages.
Calhoon, J.H. et al., "Twelve-Hour Canine Heart Preservation With a Simple, Portable Hypothermic Organ Perfusion Device", Ann. Thorac. Surg., 62:91-3 (1996), 3 pages.
Canelo R. et al., "Experience with Hystldlne Tryptophan Ketoglutarate Versus University Wisconsin Preservation Solutions in Transplatation", Int. Surg. 88(3):145-51 (2003), 8 pages.
Carrier, B., "Chapter 4: Hypoxia and Oxygenation", Alaska Air Medical Escort Training Manual, Fourth Edition, pp. 71-82, 2006, 12 pages.
Chambers, D.J. et al., "Long-Term Preservation of the Heart: The Effect of Infusion Pressure During Continuous Hypothermic Cardioplegia", The Journal of Heart and Lung Transplantation, 11(4):665-75(1992), 11 pages.
Chen, F. et al., "Development of New Organ Preservation Solutions in Kyoto University", Yonsei Medical Journal, 46(6):1107-40 (2004), 8 pages.
Chien, S. et al., "A simple technique for multiorgan preservation", The Journal of Thoracic and Cardiovascular Surgery, 95(1):55-61 (1988), 7 pages.
Chien, S. et al., "Canine Lung Transplantation After More than Twenty-four Hours of Normothermic Preservation", The Journal of Heart and Lung Transplantation, 16:340-51 (1997), 12 pages.
Chien, S. et al., "Functional Studies of the Heart During a 24-Hour Preservation Using a New Autoperfusion Preparation", The Journal of Heart and Lung Transplantation, 10(3):401-8 (1991), 8 pages.
Chinchoy, Edward Cheng-wey; "The Development, Refinement, and Uses of a Physiologically Working Isolated Ex Vivo Swine Heart Model", A thesis submitted to the Faculty of the Graduate School of the University of Minnesota, Dec. 1999 (136 pages).

(56) References Cited

OTHER PUBLICATIONS

Christophi, C. et al., "A Comparison of Standard and Rapid Infusion Methods of Liver Preservation During Multi-Organ Procurement", Aust. N.Z.J. Surg., 61(9):692-694 (1991), 3 pages.
Cimino, Adria, "Doctor develops device to preserve donated organs", Mass High Tech (2001), 2 pages.
CNN.com, "Heart kept beating outside body", Associated Press CNN News Health Section (Oct. 7, 2001, 02:59) (CNN.com/Health with WebMD.com), 2 pages.
Collins, B.H., "Organ Transplantation: What Is the State of the Art?", Annals of Surgery, 238(6 Suppl):S72-S89 (2003), 18 pages.
Cronin, D.C. et al., "Chapter 21: Liver Transplantation at The University of Chicago", Clinical Transplants 231-238 (1999), 9 pages.
Daemen, J.H.C. et al., "Short-term outcome of kidney transplants from non-heart-beating donors after preservation by machine perfusion", Transpl. Int. 9(Supp 1):S76-S80 (1996), 5 pages.
Definition of Examine, Merriam-Webster Dictionary on-line. www.merriam-webster.com/dictionary/examine, Printed Feb. 9, 2011, (1 page).
Demertzis, S. et al., "University of Wisconsin Versus St. Thomas' Hospital Solution for Human Jonor Heart Preservation", Ann Thorac Surg 55:1131-7 (1993), 7 pages.
Den Butter, G. et al., "Comparison of solutions for preservation of the rabbit liver as tested by isolated perfusion", Transpl. Int. 8(6):466-471 (1995), 6 pages.
Denham, B.S. et al., "Twenty-Four Hour Canine Renal Preservation by Pulsatile Perfusion, Hypothermic Storage, and Combinations of the Two Methods", Transplantation Proceedings, 9(3):1553-1556 (1977), 4 pages.
Dobrian, A. et al., "In vitro formation of oxidatively-modified and reassembled human low-density lipoproteins: antioxident effect of albumin", Biochimica et Biophysica Acta (BBA) 1169:12-24 (1993), 13 pages.
Drexler, H. et al., "Effect of L-arginine on coronary endothelial function in cardiac transplant recipients. Relation to vessel wall morphology," Circulation 89(4):1615-1623 (1994) (10 pages).
Egan, T. M. et al., "Ex Vivo Evaluation of Human Lungs for Transplant Suitability", Ann Thorac Surg, vol. 81, No. 4, pp. 1205-1213 (Apr. 2006) (9 pages).
Eiseman, B. et al., "Adisposable liver perfusion chamber", Surgery 60(6):1183-1186 (1966), 4 pages.
Engelman,R.M. et al., "Influence of Steroids on Complement and Cytokine Generation After Cardiopulmonary Bypass", Ann Thorac Surg 60(3):801-04 (1995) (4 pages).
European Extended Search Report issued in EP 16844964.3, dated Apr. 26, 2019 (7 pages).
European Search Report for European Patent Application No. 08795820.3 dated Apr. 17, 2014 (6 pages).
European Search Report for European Patent Application No. 09707471.0 dated May 27, 2014 (7 pages).
European Search Report for European Patent Application No. 12770852.7 dated Sep. 23, 2014. 8 pages.
Extended European Search Report issued in EP15803127.8, dated May 22, 2018 (14 pages).
Extended European Search Report issued in European Application No. 17172411.5, dated Nov. 8, 2017 (7 pages).
Fabregas, Luis, "UPMC tests machine to aid heart transplants", Pittsburg Tribune-Review (Feb. 24, 2002), (<http://www.pittsburghlive.com/x/pittsburghrib/print_19181.html<), 2 pages.
Faggian, G. et al., "Donor Organ Preservation in High-Risk Cardiac Transplantation", Transplantation Proceedings 36:617-619 (2004), 3 pages.
Featherstone, R.L. et al. "Comparison of Phosphodiesterase Inhibitors of Differing Isoenzyme Selectivity Added to St. Thomas' Hospital Cardioplegic Solution Used for Hypothermic Preservation of Rat Lungs", Am J Respir Crit Care Med, Mar. 2000,162(3):850-856 (7 pages).
Fehrenberg, C. et al., "Protective Effects of B2 Preservation Solution in Comparison to a Standard Solution (Histidine-Tryptophan-Ketoglutarate/Bretschneider) in a Model of Isolated Autologous Hemoperfused Porcine Kidney", Nephron Physiol 96:52-58 (2004) (7 pages).
Ferrera, R. et al., "Comparison of Different Techniques of Hypothermic Pig Heart Preservation", Ann Thorac Surg 57(5):1233-1239 (1994), 7 pages.
File History for U.S. Appl. No. 60/616,835, filed Oct. 7, 2004 (82 pages).
File History for U.S. Appl. No. 60/694,971, filed Jun. 28, 2005 (280 pages).
File History for U.S. Appl. No. 60/725,168, filed Oct. 6, 2005 (699 pages).
Finn, A. et al., "Effects of Inhibition of Complement Activation Using Recombinant Soluble Complement Receptor 1 on Neutrophil CD11B/CD18 and L-Selectin Expression and Release of Interleukin-8 and Elastase in Simulated Cardiopulmonary Bypass", J Thorac Cardiovasc Surg 111(2):451-459 (1996), 9 pages.
Fourcade, C. et al., "Nouvelle Méthode De Conservation Du Rein Avec Une Solution De Collins", <<A New Method of Kidney Preservation with Collins' Solution,>> Biomed. 21(7):308-11 (1974), English Abstract, 5 pages.
Fraser, C.D. Jr. et al., "Evaluation of Current Organ Preservation Methods for Heart-Lung Transplantation", Transplantation Proceedings, 20(1 Suppl. 1):987-990 (1988), 4 pages.
Glucose, The Merck Index, 11th ed. Entry 4353 (pp. 699-700) (1989), 3 pages.
Grynberg, A. et al., "Fatty Acid Oxidation in the Heart", Journal of Cardiovascular Pharmacology, 28(Suppl. 1):S11-S17 (1996) (8 pages).
Guarrera, J.V. et al., "Pulsatile Machine Perfusion With Vasosol Solution Improves Early Graft Function After Cadaveric Renal Transplantation", Transplantation 77(8):1264-1268 (2004), 5 pages.
Gundry, S.R. et al., "Successful Transplantation of Hearts Harvested 30 Minutes After Death From Exsanguination", Ann Thorac Surg 53(5):772-775 (1992), 4 pages.
Habazetti, H. et al., "Improvement in Functional Recovery of the Isolated Guinea IG Heart After Hyperkalemic Reperfusion With Adenosine", J Thorac Cardiovasc Surg 111(1):74-84 (1996) (11 pages).
Hachida, M. et al., Abstract "Efficacy of myocardial preservation using HTK solution in continuous 120 min cross-clamping method—a comparative study with GIK method", Nippon Kyobu Geka Gakkai Zasshi. 41(9):1495-1501 (1993), 1 page.
Hardesty, R.L. et al., Original Communications, "Autoperfusion of the heart and lungs for preservation during distant procurement", J Thorac Cardiovasc Surg, 93:11-18 (1987) (8 pages).
Hartman, J.C., "The Role of Bradykinin and Nitric Oxide in the Cardioprotective Action of ACE Inhibitors", Ann Thorac Surg 60:789-792 (1995), 4 pages.
Hassanein, W.H. et al., "A Novel Approach for 12 Hour Donor Heart Preservation, Presented at the 70th Scientific Sessions of The American Heart Association", Abstract was published in Circulation (1997), 1 page.
Hassanein,W.H. et al. "Continuous Perfusion of Donor Hearts in the Beating State Extends Preservation Time and Improves Recovery of Function", The Journal of Thoracic and Cardiovascular Surgery, pp. 821-830 (1998), 10 pages.
Heil, J.E. et al., "A Controlled Comparison of Kidney Preservation by Two Methods: Machine erfusion and Cold Storage", Transplantation Proceedings 19(1):2046 (1987), 1 page.
Howarth, F.C. et al., "Effects of extracellular magnesium and beta adrenergic stimulation on contractile force and magnesium mobilization in the isolated rat heart", Magnesium Research, 7:187-197, 1994 (13 pages).
Hülsmann, W.C et al., "Loss of cardiac contractility and severe morphologic changes by acutely lowering the pH of the perfusion medium: protection by fatty acids", Bragen 20256, Biochimica et Biophysica Acta., 1033:214-218 (1990) (5 pages).
Ida, K. "Titanium for Medical and Dental Use", Japanese journal of medical electronics and biological engineering, 24(1):47-54,1986 (12 pages)—with English Summary.
Imber, C. et al., "Advantages of Normothermic Perfusion Over Cold Storage in Liver Preservation", Transplantation, 73(5):701-709 (2002), 9 pages.

(56) References Cited

OTHER PUBLICATIONS

International Search Report and Written Opinion for International Application No. PCT/US2012/033626 dated Sep. 20, 2012 (12 pages).
International Search Report and Written Opinion issued by the U.S. Patent and Trademark Office as Searching Authority, in International Application No. PCT/US16/50512, dated Dec. 12, 2016 (9 pages).
International Search Report, issued by the European Patent Office as Searching Authority, in PCT/US07/009652 International Search Report, dated Apr. 18, 2008, 5 pages.
International Search Report, issued by the European Patent Office as Searching Authority, issued in PCT/US98/19912, dated May 3, 1999 (4 pages).
International Search Report, issued by the U.S. Patent Office as Searching Authority, issued in PCT/US08/61454 International search report dated Dec. 5, 2008 (2 pages).
International Search Report, issued by the U.S. Patent Office as Searching Authority, issued in PCT/US09/032619, dated Jun. 4, 2009 (4 pages).
Janßen, H. et al., "UW is Superior to Celsiorand HTK in the Protection of Human Liver Endothelial Cells Against Preservation Injury", Liver Transplantation, 10(12):1514-1523 (2004), 10 pages.
Johnson, Kerry et al., "POPS: Portable Organ Preservation System", UPMC Health System and TransMedics, Inc. (No date) (1 page).
Johnston, R., "What's Normal About DLCO?", PFT Blog, Jan. 1, 2014 (17 pages).
Kawakami, et al., "Successful Preservation of the Isolated Canine Heart for 24 Hours by Low Pressure-Low Temperature Continuous Perfusion", Japanese Annals of Thoracic Surgery, Japan, 7(6):543-547, Dec. 25, 1987 (13 pages)—English Translation.
Kawamura, T. et al., "Long-Term Preservation of Canine Pancreas By a New Simple Cold Storage Method Using Perfluorochemical—The Two-Layer Cold Storage Method (Euro-Collins' Solution/Perfluorochemical)—", Kobe J. Med. Sci., 38(2):135-145 (1992), 11 pages.
Kelly, R.F., "Current strategies in lung preservation", J. Lab Clin Med, 136:427-440 (2000), 14 pages.
Keshavjee, S.H. et al., "A method for safe twelve-hour pulmonary preservation", J Thorac Cardiovasc Surg, 98:529-534 (1989), 6 pages.
Kioka, Y. et al., "Twenty-Four-Hour Isolated Heart Preservation by Perfusion Method With Oxygenated Solution Containing Perfluorochemicals and Albumin", The Journal of Heart Transplantation, 5:437-443 (1986), 7 pages.
Koike, et al., "An Experimental Study on the Hypothermic Preservation of the Rabbit Heart Using Glucose-Insulin-Potassium Solution—Intermittent Perfusion Method Versus Simple Immersion Method", Japanese Annals of Thoracic Surgery, 7(6):527-532, Dec. 25, 1987 (16 pages)—English Translation.
Kozaki, K. et al., "Usefulness of a Combination of Machine Perfusion and Pentoxifylline for Porcine Liver Transplantation From Non-Heart-Beating Donors With Prolonged Hypotension", Transplantation Proceedings, 29:3476-3477 (1997), 2 pages.
Kubono, K. et al., "Examination of Plasma and Corpuscle Adenosine Concentration in Normal Subject by Radioimmunoassay", Rinshou Kagaku (Clinical Chemistry, 20(2):72-77, Jun. 1991 (6 pages)—Japanese Language.
Kuroda, Y. et al., "A New, Simple Method for Cold Storage of the Pancreas Using Perfluorochemical", Transplantation, 46(3):457-460 (1988), 4 pages.
Lasley, R.D. et al., "Protective Effects of Adenosine in the Reversibly Injured Heart", Ann Thorac Surg, 60(3):843-846 (1995), 4 pages.
Lawrence, C., "Machine preserves organs outside body," Chicago Sun Times (2001), 1 page.
Lefer, A.M., "Attenuation of Myocardial Ischemia-Reperfusion Injury With Nitric Oxide Replacement Therapy", Ann Thorac Surg 60(3):847-851 (1995), 5 pages.

Li, G. et al., "Functional Recovery in Rabbit Heart after Preservation with a Blood Cardioplegic Solution and Perfusion," J Heart Lung Transplant, 12(2)263-270 (1993) (8 pages).
Li, X. et al., "Insulin in University of Wisconsin Solution Exacerbates the Ischemic Injury and Decreases the Graft Survival Rate in Rat Liver Transplantation", Transplantation, 15:76(1):44-49 (2003), 6 pages.
Li, X. et al., "Insulin in UW Solution Exacerbates Hepatic Ischemia / Reperfusion Injury by Energy Depletion Through the IRS-2 / SREBP—1c Pathway", Liver Transplantation, 10(9):1173-1182 (2004), 10 pages.
Liu,J. et al., "Annexin V Assay-proven Anti-apoptotic Effect of Ascorbic Acid 2-glucoside after Cold Ischemia/Reperfusion Injury in Rat Liver Transplantation", Acta Med. Okayama, 57(5):209-216 (2003), 8 pages.
Macchlarini, P. et al. "Ex Vivo Lung Model of Pig-To-Human Hyperacute Xenograft Rejection", The Journal of Thoracic and Cardiovascular Surgery, 114:3, 315-325 (1997) (11 pages).
Mankad, P. et al., "Endothelial dysfunction caused by University of Wisconsin preservation solution in the rat heart", J Thorac Cardiovasc Surg 104(6): 1618-1624 (1992), 7 pages.
Matsuno, N. et al., "Effectiveness of Machine Perfusion Preservation as a Viability Determination Method for Kidneys Procured from Non-Heart-Beating Donors," Transplantation Proceedings, 26(4):2421-2422 (1994) (2 pages).
Matsuno, N. et al., "The Effect of Machine Perfusion Preservation Versus Cold Storage on the Function of Kidneys From Non-Heart-Beating Donors", Transplantation, 57(2):293-294 (1994) (2 pages).
Menasché, P. et al., "Experimental evaluation of Celsior®, a new heart preservation solution," Eur J Cardio-thorac Surg 8:207-213 (1994), 7 pages.
Menasché, P. et al., "Improved recovery of heart transplants with a specific kit of preservation solutions," The Journal of Thoracic and Cardiovascular Surgery, 105(2):353-363 (1993), 11 pages.
Menasché, P., "The inflammatory response to cardiopulmonary bypass and its impact on postoperative myocardial function", Current Opinion in Cardiology, 10:597-604 (1995) (8 pages).
Moisiuk, Y. et al., "Histidine-Tryptophan-Ketoglutarate Versus Euro-Collins for Preservation of Kidneys From Non-Heart-Beating Donors", Transplantation Proceedings, 28(1):202 (1996) (1 page).
Moller-Pedersen, T. et al., "Evaluation of potential organ culture media for eye banking using human donor corneas", Br J Ophthamol, 85(9):1075-1079 (2001), 5 pages.
Morimoto, T. et al., "A Simple Method for Extended Heart-Lung Preservation by Autoperfusion", Trans Am Soc Artif Intern Organs, 30:320-324 (1984), 5 pages.
Nicholson, M.L. et al., "A Comparison of Renal Preservation by Cold Storage and Machine Perfusion Using a Porcine Autotransplant Model", Transplantation 78(3):333-337 (2004), 5 pages.
No Author Listed, "Custodiol® HTK Solution for Multi-Organ Protection", Saudi Center for Organ Transplantation, Date Unknown, originally cited to U.S. Patent Office Jun. 30, 2014, in U.S. Appl. No. 12/892,451 (2 pages).
No Author Listed, "Soltran Kidney perfusion fluid", Baxter, No Month Listed—2001-2004 (1 page).
No Author Listed, "The comprehensive resource for physicians, drug and illness information", ViaSpan™ DuPont Pharma Cold Storage Solution, Date Unknown (3 pages).
No Author Listed, "UW Solution Composition", DuPont Pharmaceutical, Date Unknown (1 page).
No Author Listed. "Custodiol HTK" Physicians' Desk Reference, 57th Edition, Thomson PDR. ISBN:1-56363-445-457. No Month Listed—2003 (3 pages).
Odagiri, Shigetoh et al. "New Pulsatile Pump Using Pulsatile Assist Device-Hemodynamic Comparison of Pulsatile V-A Bypass (VABP), Pulsatile Left Hear ByPass (LHBP) and Constant Flow Left Heart Bypass (LHB)." Journal of Japan Surgical Society. V83, No Month Listed 1983. pp. 515-523, 12 pages.
Opelz, G. et al., "Advantage of Cold Storage Over Machine Perfusion for Preservation of Cadaver Kidneys", Transplantation, 33(1):64-68 (1982), 5 pages.
Opelz, G. et al., "Comparative Analysis of Kidney Preservation Methods", Transplantation Proceedings 28(1):87-90 (1996), 4 pages.

(56) References Cited

OTHER PUBLICATIONS

Ota et al. "Artificial Organ-Current State and Future of Substitution of Functions." No Month Listed 1983. pp. 150-151, 4 pages.
Pearl, J.M. et al., Loss of endothelium-dependent vasodilatation and nitric oxide release after myocardial protection with University of Wisconsin solution, Cardiovascular Surgery 107(1):257-264 (1994) (8 pages).
Petrovsky, B.V. et al., "Justification and Application of a New Method for Transorganic Oxygen Preservation of the Kidneys", Vestn. Akad. Med. Nauk, SSSR., (2):69-82 (1989)—English Abstract, 15 pages.
Pinsky, D. et al., "Restoration of the cAMP Second Messenger Pathway Enhances Cardiac Preservation for Transplantation in a Heterotopic Rat Model", J. Clin. Invest. 92(6):2944-3002 (1993) (9 pages).
Ploeg, R.J. et al., "Successful 72-Hour Cold Storage of Dog Kidneys With UW Solution", Transplantation, 46(2):191-196 (1988), 6 pages.
Pokorny, H. et al., "Histidine-tryptophan-ketoglutarate solution for organ preservation in human liver transplantation—a prospective multi-centre observation study", Transpl Int 17(5):256-260 (2004), (5 pages).
Poston, R.S. et al., "Optimizing Donor Heart Outcome After Prolonged Storage With Endothelial Function Analysis and Continuous Perfusion", Ann Thorac Surg, 78:1362-1370, 2004 (9 pages).
Potdar, S. et al., "Initial experience using histidine-tryptophan-ketoglutarate solution in clinical pancreas transplantation", Clin Transplant, 18(6):661-665 (2004), 5 pages.
Pozniak, A., "Keeping Hearts Alive Doctors Develop a High-Tech System to Salvage Donated Organs", ABC News.com, (Dec. 7, 2001) (<http://abcnews.go.com/print?id=117085>), (2 pages).
Probst, R. et al. "Carbohydrate and fatty acid metabolism of cultured adult cardiac myocytes", Am. J. Physiol. 250 (Heart, Circ. Physiol. 19):H853-H860 (1986) (8 pages).
Pruitt, "Pharmacological Treatment of Respiratory Disorders", RT Magazine, http://www.rtmagazine.com/2007/05/pharmacological-treatment-of-respiratory-disorders, May 3, 2007, accessed Jan. 1, 2019 (6 pages).
Rao, V. et al., "Donor Blood Perfusion Improves Myocardial Recovery After Heart Transplantation", J. Heart Lung Transplant. 16(6):667-673 (1997) (7 pages).
Reddy, S.P. et al., "Preservation of Porcine Non-Heart-Beating Donor Livers by Sequential Cold Storage and Warm Perfusion", Transplantation, 77(9):1328-1332 (2004), 5 pages.
Richens, D. et al., "Clinical Study of Crystalloid Cardiplegia vs Aspartate-Enriched Cardioplegia Plus Warm Reperfusion for Donor Heart Preservation", Transplantation Proceedings 24(1): 1608-1610 (1993) (3 pages).
Rinder, C.S. et al., "Blockade of C5a and C5b-9 Generation Inhibits Leukocyte and Platelet Activation during Extracorporeal Circulation", J. Clin. Invest. 96:3(1564-1572) 1995 (9 pages).
Rosenkranz, E.R., "Substrate Enhancement of Cardioplegic Solution: Experimental Studies and Clinical Evaluation", Ann Thorac Surg 60:797-800 (1995) (4 pages).
Rossi, L., "Portable Organ Preservation System™ Keeps Human Heart Alive Outside Body", PITT Campaign Chronicle (Oct. 7, 2001), 2 pages.
Rossi, L., et al., Innovations-Report "New Organ Preservation Solution Easier To Use," (<http://www.innovations-report.de/specials/printa.php?id=18854.html>) Feb. 6, 2003, printed Jul. 21, 2006, 2 pages.
Saez, D.G. et al., "Evaluation of the Organ Care System in Heart Transplantation With an Adverse Donor/Recipient Profile", Ann. Thorac. Surg., 98:2099-2106, 2014 (8 pages).
Sato, H. et al., "Supplemental L-Arginine During Cardioplegic Arrest and Reperfusion Avoids Regional Postischemic Injury", J Thorac Cardiovasc Surg 110(2):302-314 (1995), 13 pages.
Schmid, T. et al., "The Use of Myocytes as a Model for Developing Successful Heart Preservation Solutions", Transplantation 52(1):20-26 (Jul. 1991) (7 pages).

Schon, M.R. et al., "Liver Transplantation After Organ Preservation With Normothermlc Extracorporeal Perfusion", Annals of Surgery 233(1):114-123 (2001), 10 pages.
Schwalb, H. et al., "New Solution for Prolonged Myocardial Preservation for Transplantation", The Journal of Heart and Lung Transplantation 17(2):222-229 (1998), 8 pages.
Seccombe, J.F. et al., "Coronary Artery Endothelial Function After Myocardial Ischemia and Reperfusion", Ann Thorac Surg 60(3):778-788 (1995), 11 pages.
Segel, L.D. et al., "Posttransplantation Function of Hearts Preserved with Fluorochemical Emulsion", J Heart Lung Transplant, 13(4):669-680 (1994), 12 pages.
Segel,L.D. et al., "Recovery of Sheep Hearts After Perfusin Preservation or Static Storage with Crystalloid Media", The Journal of Heart and Lung Transplantation, 17:211-221 (1998) (11 pages).
Sekine, M. et al., "Effect of Obese and Aging on Blood Fatty Acid Consumption in Japanese", Bulletin of the Graduate School of Human Life Science, Showa Women's University, 4:63-70, 1995 (8 pages)—English Abstract.
Semat, H. and Katz, R., "Physics, Chapter 9: Hydrodynamics (Fluids in Motion)", Hydrodynamics. University of Nebraska—Lincoln. Pap143. No Month Listed 1958 (18 pages).
Shimokawa, S. et al., "A New Lung Preservation Method of Topical Cooling by Ambient Cold Air Combined with High-Frequency Oscillation: An Experieental Study", Transplantation Proceedings, 26(4):2364-2366 (1994) (3 pages).
Shimokawa, S. et al., "A New Lung Preservation Method of Topical Cooling by Ambient Cold Air: An Experimental Study", Transplantation Proceedings, 23 (1):653-654 (1991) (2 pages).
Shirakura, R. et al., "Multiorgan Procurement from Non-Heart-Beating Donors by use of Osaka University Cocktail, Osaka Rinse Solution, and the Portable Cardiopulmonary Bypass Machine", Transplantation Proceedings, 25(6):3093-3094 (1993) (2 pages).
Southard, J., "The Right Solution for Organ Preservation", Business Briefings: Global Surgery 79-84 (2004) (6 pages).
Steen, Stig et al. "Transplantation of Lungs from Non-Heart-Beating Donors After Functional Assessment Ex Vivo." The Annals of Thoracic Surgery. Elsevier Inc. No Month Listed 2003. vol. 76, pp. 244-252.
Stubenitsky, B.M. et al., "Kidney preservation in the next millenium". Transpl Int, 12:83-91 (1999), 9 pages.
Sunamori, M. et al., "Relative Advantages of Nondepolarizing Solution to Depolarizing University of Wisconsin Solution in Donor Heart Preservation", Transplantation Proceedings, 25(1): 1613-1617 (1993), 5 pages.
Synchrony Definition, http://dictionary.reference.com/browse/synchrony, Random House Unabridged Dictionary, 2006 (1 page).
Tang, D.G. et al., "Warm Ischemia Lung Protection With Pinacidil: An ATP Regulated Potassium Channel Opener", Ann Thorac Surg, 76:385-390 (2003), 6 pages.
Tesi, R.J. et al., Pulsatile Kidney Perfusion for Preservation and Evaluation: Use of High-Risk Kidney Donors to Expand the Donor Pool, Transplantation Proceedings, 25(6):3099-3100 (1993) (2 pages).
Turpin, B.P. et al., "Perfusion of Isolated Rat Adipose Cells", The Journal of Clinical Investigation, 60:442-448 (1977), 7 pages.
U.S. Food and Drug Administration, Center for Drug Evaluation and Research, "Drugs@FDA—Solu-Medrol: Label and Approval History", (Available online at http://www.accessdata.fda.gov/scripts/cder/drugsatfda/index.cfm?fuseaction=Search.Label_ApprovalHistory#apphist . . . ), accessed Feb. 9, 2010 (3 pages).
U.S. Food and Drug Administration, Center for Drug Evaluation and Research, "Drugs@FDA—Solu-Medrol: Drug Details", (Accessible online at http://www.accessdata.fda.gov/scripts/cder/drugsatfda/index.cfm?fuseaction=Search.DrugDetails . . . ), accessed Feb. 9, 2010 (1 page).
Vinten-Johansen, J. et al., "Reduction In Surgical Ischemic-Reperfusion Injury With Adenosine and Nitric Oxide Therapy", Ann Thorac Surg 60(3):852-857 (1995), 6 pages.
Voiglio, E. et al. "Rat Multiple Organ Blocks: Microsurgical Technique of Removal for Ex Vivo Aerobic Organ Preservation Using a Fluorocarbon Emulsion", Microsurgery 20:3, 109-115 (2000) (7 pages).

(56) References Cited

OTHER PUBLICATIONS

Watanabe, S. et al., "Effects of free fatty acids on the binding of bovine and human serum albumin with steroid hormones", Biochimica et Biophysica Acta (BGBA), 1289:385-396 (1996), 12 pages.
Wei, Z., et al., "A Study on the Preservation of Rat Kidney with HX-III Solution", J WCUMS, 31(3):347-349 (2000)—English Abstract, 4 pages.
Wicomb, W. et al., "Orthotopic transplantation of the baboon heart after 20 to 24 hours' preservation by continuous hypothermic perfusion with an oxygenated hyperosmolar solution", J. Thorac Cardiovasc Surg, 83(1):133-140 (1982), 8 pages.
Wicomb, W.N. et al., "24-Hour Rabbit Heart Storage With UW Solution", Transplantation, 48(1):6-9 (1989), 4 pages.
Wicomb, W.N. et al., "Cardiac Transplantation Following Storage of the Donor Heart by a Portable Hypothermic Perfusion System", The Annals of Thoracic Surgery, 37(3):243-248 (1984), 6 pages.
Wright, N. et al. "A porcine ex vivo paracorporeal model of lung transplantation", Laboratory Animals Ltd. Laboratory Animals, 34:1, 56-62 (2000) (7 pages).
Yang, W. et al., "Effect of Hypoxia and Reoxygenation on the Formation and Release of Reactive Oxygen Species by Porcine Pulmonary Artery Endothelial Cells", Journal of Cellular Physiology, 164:414-423 (1995) (10 pages).
Yeung, J., et al., "Physiologic assessment of the ex vivo donor lung for transplantation", Journal of Heart and Lung Transplantation, 31(10):1120-1126, Oct. 2012 (7 pages).
Yland, M.J. et al., "New Pulsatile Perfusion Method for Non-Heart-Beating Cadaveric Donor Organs: A Preliminary Report", Transplantation Proceedings, 25(6):3087-3090 (1993), 4 pages.
Yokoyama, H. et al., "Isolated Dog Hearts Prepared in Cold Tyrode Solution and Reperfused with Arterial Blood are Functionally and Ultrastructurally Normal", The Tohoku Journal of Experimental Medicine, 156:121-134, 1988 (14 pages).
Zhang, Z. et al., "Research Progress on Preservation of Severed Limbs", Chinese Journal of Reparative and Reconstructive Surgery, 14(3):189-192 (2000)—English Abstract, 8 pages.
Jirsch, D.W. et al., "Ex Vivo Evaluation of Stored Lungs", The Annals of Thoracic Surgery, 10(2):163-168, Aug. 1970 (6 pages).
Venuta, F. et al., "History of lung transplantation", Journal of Thoracic Disease, 9(12):5458-5471, Dec. 2017 (14 pages).
Chen, E. P. et al., "Milrinone Improves Pulmonary Hemodynamics and Right Ventricular Function in Chronic Pulmonary Hypertension", Ann Thorac Surg, 63:814-821, 1997 (8 pages).
Duarte, J.D. et al., "Pharmacologic treatments for pulmonary hypertension: exploring pharmacogenomics", Future Cardiol., 9(3):335-349, 2013 (15 pages).
Givertz, M.M. et al., "Effect of Bolus Milrinone on Hemodynamic Variables and Pulmonary Vascular Resistance in Patients With Severe Left Ventricular Dysfunction: A Rapid Test for Reversibility of Pulmonary Hypertension", JACC, 28(7):1775-1780, Dec. 1996 (6 pages).
Han, B. et al., "Study on the clinical efficacy of specific phosphodiesterase inhibitor in patients with pulmonary hypertension due to left heart disease", Experimental and Therapeutic Medicine, 16:1175-1186, 2018 (12 pages).
Hoeper, M.M. et al., "Intensive Care Unit Management of Patients with Severe Pulmonary Hypertension and Right Heart Failure", Am J Respir Crit Care Med, 184:1114-1124, 2011 (11 pages).
Hui-Li, G. "The Management of Acute Pulmonary Arterial Hypertension", Cardiovascular Therapeutics, 29:153-175, 2011 (23 pages).
Jaski, B.E. et al., "Positive inotropic and vasodilator actions of milrinone in patients with severe congestive heart failure. Dose-response relationships and comparison to nitroprusside", J. Clin Invest., 75(2):643-649, 1985 (8 pages).
Lobato, E.B. et al., "Treatment with phosphodiesterase inhibitors type III and V: milrinone and sildenafil is an effective combination during thromboxane-induced acute pulmonary hypertension", British Journal of Anaesthesia, 96(3):317-322, 2006 (6 pages).
Open Anesthesia—Milrinone: pharmacology, https://www.openanesthesia.org/milrinone_pharmacology/, accessed 2019 (3 pages).

Siobal, M.S. "Pulmonary Vasodilators", RespirCare, 52(7):885-899, Jul. 2007 (15 pages).
Russell, H.E. et al., "An Evaluation of Infusion Therapy (Including Dextran) for Venous Thrombosis", Circulation, 33:839-846, Jun. 1966 (8 pages).
Baker, L.E. et al., "Artificial Maintenance Media for Cell and Organ Cultivation", Journal of Experimental Medicine, 70:29-38, Jul. 1, 1939 (15 pages).
Rao, M.V. et al., "Magnesium Sulfate: Chemical and Technical Assessment", MgSO4 (CTA), 2007 (5 pages).
European Search Report issued for European Application No. EP19204566.4, dated May 25, 2020 (7 pages).
Gohrbandt, B., et al., "Glycine intravenous donor preconditioning is superior to glycine supplementation to low-potassium dextran flush preservation and improves graft function in a large animal lung transplantation model after 24 hours of cold ischemia", Journal of Thoracic and Cardiovascular Surgery, 131(3):724-729, Mar. 2006 (6 pages).
European Extended Search Report issued in EP20206681.7, dated Apr. 26, 2021 (8 pages).
Andreasson, et al., "Ex vivo lung perfusion in clinical lung transplantation - State of the art", European Journal of Cardio-Thoracic Surgery, 46:779-788, 2014 (10 pages).
Becker, et al., "Evaluating acellular versus cellular perfusate composition during prolonged ex vivo lung perfusion after initial cold ischaemia for 24 hours", Transplant International, 29:88-97, 2016, published online Aug. 27, 2015 (10 pages).
FDA Premarket Approval 510k (extracts), "Perfadex® Solution for Lung Perfusion", dated Mar. 8, 2001 (61 pages).
FDA Premarket Approval 510k, "Perfadex® with THAM", dated Oct. 9, 2008 (5 pages).
FDA Summary of Safety and Probable Benefit, "XVIVO Perfusion System (XPS™) with STEEN Solution TM Perfusate", HUD Designation No. 08-0194, Notice of Approval dated Aug. 12, 2014 (52 pages).
Fisher, et al., "An observational study of Donor Ex Vivo Lung Perfusion in UK lung transplantation: DEVELOP-UK", Health Technology Assessment, vol. 20, No. 85, Nov. 2016 (310 pages).
Ingemansson, et al., "Importance of Calcium in Long-Term Preservation of the Vasculature", Ann Thorac Surg, 61:1158-1162, 1996 (5 pages).
Loor, et al., "Prolonged EVLP Using OCS Lung: Cellular and Acellular Perfusates", Author Manuscript published in final edited form as Transplantation, 101(10):2303-2311, Oct. 2017 (20 pages).
Munshi, et al., "Donor management and lung preservation for lung transplantation", Lancet Respir Med, 1:318-328, published online Feb. 20, 2013 (11 pages).
Pego-Fernandes, et al., "Ex vivo lung perfusion: initial Brazilian experience", J. Bras. Pneumol., 35(11): 1107-1112, 2009 (6 pages).
Perfadex Guidelines, Nhs Cardiothoracic Advisory Group (CTAG), Mar. 2016 (2 pages).
Steen Solution, Consultation Procedure Public Assessment Report (CPAR), European Medicines Agency, EMEA/CHMP/329441/2005, Aug. 8, 2012 (20 pages).
Wallinder, et al., "Transplantation of initially rejected donor lungs after ex vivo lung perfusion", Cardiothoracic Transplantation, 144(5):1222-1228, Nov. 2012 (7 pages).
Xvivo Perfusion, RedEye Equity Research, May 29, 2020 (3 pages).
Zalewska, et al., National Standards for Organ Retrieval from Deceased Donors (extracts), NHS Blood and Transplant, UK National Health Service, MPD1043/8, effective date Oct. 15, 2018 (50 pages).
Rega, et al., "Long-term Preservation With Interim Evaluation of Lungs From a Non-Heart- Beating Donor After a Warm Ischemic Interval of 90 Minutes", Annals of Surgery, 238(6):782-793, Dec. 2003 (12 pages).
Wittwer, et al., "Experimental Lung Transplantation: Impact of Preservation Solution and Route of Delivery", The Journal of Heart and Lung Transplantation, 24(8): 1081-1090, Aug. 2005 (10 pages).
Asparagine, Encyclopedia.com, https://www.encyclopedia.com/science-and-technology/biochemistry/biochemistry/asparagine, accessed May 7, 2022 (3 pages).

(56) References Cited

OTHER PUBLICATIONS

Cysteine, Encyclopedia.com, https://www.encyclopedia.com/science-and-technology/biochemistry/biochemistry/cysteine, accessed May 7, 2022 (4 pages).
European Commission, Scientific Committee on Food, "Opinion on Substances for Nutritional Purposes Which Have Been Proposed for Use in the Manufacture of Foods for Particular Nutritional Purposes ('Parnuts')", SCF/CS/ADD/NUT/20/Final, http://www.europa.eu.int/comm/dg24/health/sc/scf/index_en.html, Dec. 5, 1999 (19 pages).
European Extended Search Report issued in European Patent Application No. 22158928.6. dated Jun. 29, 2022 (13 pages).
Glutamine, Encyclopedia.com, https://www.encyclopedia.com/science-and-technology/biochemistry/biochemistry/glutamine, accessed May 7, 2022 (7 pages).
Albes, et al., "Influence of the Perfusate Temperature on Lung Preservation: Is There an Optimum?", European Surgical Research, 29:5-11, 1997 (7 pages).
Besterman, et al., "Regulation of protein synthesis in lung by amino acids and insulin", American Journal of Physiology: Endocrinology and Metabolism, 245(5): E508-E514, Nov. 1, 1983 (7 pages).
Erasmus, et al., "Normothermic ex vivo lung perfusion of non-heart-beating donor lungs in pigs: from pretransplant function analysis towards a 6-h machine preservation", Transplant International, 19(7):589-593, Jul. 1, 2006 (5 pages).
"The secret of the turtle", <https://mag.ebmpapst.com/en/industries/medical/the-secret--of-the-turtle_2433/>, mag: The Magazine of ebm-papst, Sep. 2009 (5 pages).
Baker, et al., "Calcium Content of St. Thomas' II Cardioplegic Solution Damages Ischemic Immature Myocardium", Annals of Thoracic Surgery, 52(4):993-999, Oct. 1991 (7 pages).
Charest, et al., "Design and validation of a clinical-scale bioreactor for long-term isolated lung culture", Author Manuscript published in Final Edited form as Biomaterials, 52:79-87, Jun. 2015 (22 pages).
De Hart, et al., "An ex vivo platform to simulate cardiac physiology: a new dimension for therapy development and assessment", The International Journal of Artificial Organs, 34(6): 495-505, Jun. 2011 (11 pages).
Dobson, et al., "Adenosine and lidocaine: A new concept in nondepolarizing surgical myocardial arrest, protection, and preservation", Journal Thoracic and Cardiovascular Surgery, 127(3):794-805, Mar. 2004 (12 pages).
Ebel, et al., "Lidocaine reduces ischaemic but not reperfusion injury in isolated rat heart", British Journal Anesthesia, 86(6):846-852, 2001 (7 pages).
Ely, et al., "Protective Effects of Adenosine In Myocardial Ischemia", Circulation, 85(3):893-904, Mar. 1992 (12 pages).
European Extended Search Report issued in European Patent Application No. 17805438.3, dated Jan. 28, 2020 (14 pages).
European Extended Search Report issued in European Application No. 13738530.8, dated Jan. 25, 2016 (9 pages).
European Extended Search Report issued in European Application No. 15775970.5, dated Oct. 24, 2017 (10 pages).
European Extended Search Report issued in European Patent Application No. 15853016.2, dated Mar. 9, 2018 (12 pages).
European Extended Search Report issued in European Patent Application No. 15867786.4, dated Feb. 8, 2019 (14 pages).
European Extended Search Report issued in European Patent Application No. 15767752.7, dated Nov. 30, 2017 (7 pages).
European Extended Search Report issued in European Patent Application No. 18879106.5, dated Dec. 17, 2020 (8 pages).
European Search Report issued in European Patent Application No. 15867786.4, dated Sep. 3, 2018 (11 pages).
Gao, et al., "Role of Troponin I Proteolysis in the Pathogenesis of Stunned Myocardium", Circulation Research, 80(3):393-399, Mar. 1, 1997 (17 pages).
Hearse, et al., "Protection of the myocardium during ischemic arrest", Journal Thoracic Cardiovascular Surgery, 81(6):873-879, Jun. 1981 (7 pages).
International Preliminary Report on Patentability issued by the Canadian Patent Office as International Searching Authority in International Application No. PCT/CA2015/051316 dated Apr. 10, 2017 (5 pages).
International Preliminary Report on Patentability issued in International Application No. PCT/CA15/50297, dated Oct. 12, 2016 (6 pages).
International Preliminary Report on Patentability issued in International Application No. PCT/CA15/51084, dated Feb. 15, 2017 (3 pages).
International Preliminary Report on Patentability, issued by Canadian Patent Office as International Searching authority, in International Application No. PCT/CA2015/050201 dated Sep. 27, 2016 (5 pages).
International Preliminary Report on Patentability, issued by Canadian Patent Office in International Application No. PCT/CA2013/000031 dated Apr. 23, 2014 (8 pages).
International Search Report and Written Opinion issued by the Canadian Patent Office as International Searching Authority in International Application No. PCT/CA2015/051316, dated mailed Mar. 16, 2016 (8 pages).
International Search Report and Written Opinion issued by Canadian Patent Office as International Searching Authority in International Application No. PCT/CA13/00031, dated Apr. 15, 2013 (9 pages).
International Search Report and Written Opinion issued by Canadian Patent Office as International Searching Authority in International Application No. PCT/CA18/51474, dated Mar. 4, 2019 (6 pages).
International Search Report and Written Opinion issued by the Canadian Patent Office as International Searching Authority in International Application No. PCT/CA15/50201, dated Jun. 10, 2015 (8 pages).
International Search Report and Written Opinion issued by the Canadian Patent Office as International Searching Authority in International Application No. PCT/CA15/50297, dated Jul. 13, 2015 (8 pages).
International Search Report and Written Opinion issued by the Canadian Patent Office as International Searching Authority in International Application No. PCT/CA15/51084, dated Feb. 5, 2016 (8 pages).
Jakobsen, et al., "Adenosine instead of supranormal potassium in cardioplegia: It is safe, efficient, and reduces the incidence of postoperative atrial fibrillation. A randomized clinical trial", Journal of Thoracic and Cardiovascular Surgery, 145(3):812-818, Mar. 2013 (7 pages).
Lim, et al., "Computational analysis of the effect of the type of LVAD flow on coronary perfusion and ventricular afterload", J. Physiol Sci., 59:307-316, 2009 (10 pages).
McHaffey, et al., "Airway pressure release ventilation during ex vivo lung perfusion attenuates injury", Journal Thoracic Cardiovascular Surgery, 153(1): 197-204, Jan. 2017 (8 pages).
Muhlbacher, et al., "Preservation Solutions for Transplantation", Transplantation Proceedings, 31(5):2069-2070, Aug. 1999 (2 pages).
Nelson, et al., "Abstract 736: Determination of Optimum Ventilation Strategy for Ex-Vivo Lung Perfusion: Comparing Negative and Positive Pressure Ventilation", Journal of Heart and Lung Transplantation, 34(4 Supplement):S270, Apr. 2015 (1 page).
O'Blenes, et al., "Protecting the aged heart during cardiac surgery: The potential benefits of del Nido cardioplegia", Journal Thoracic and Cardiovascular Surgery, 141(3):762-770, Mar. 2011 (9 pages).
Popov, et al., "Ex Vivo Lung Perfusion - State of the Art in Lung Donor Pool Expansion", Medical Science Monitor Basic Research, 21:9-14, Feb. 3, 2015 (6 pages).
Raymondos, et al., "Combined Negative- and Positive-Pressure Ventilation for the Treatment of ARDS", Case Reports in Critical Care, Article ID714902, 2015 (5 pages).
Robinson, et al., "Lowering the calcium concentration in St. Thomas' Hospital cardioplegic solution improves protection during hypothermic ischemia", Journal Thoracic and Cardiovascular Surgery, 101(2):314-325, Feb. 1991 (12 pages).
Rudd, et al., "Eight hours of cold static storage with adenosine and lidocaine (Adenocaine) heart preservation solutions: Toward thera-

(56) References Cited

OTHER PUBLICATIONS peutic suspended animation", Journal Thoracic Cardiovascular Surgery, 142(6):1552-1561, Dec. 2011 (10 pages).
Rudd, et al., "Toward a new cold and warm nondepolarizing, normokalemic arrest paradigm for orthotopic heart transplantation", The Journal of Thoracic and Cardiovascular Surgery, 137(1):198-207, Jan. 2009 (10 pages).
Sutherland, et al., "The Isolated Blood And Perfusion Fluid Perfused Heart", https://www.southalabama.edu/ishr/help/hearse/, Cardiovascular Research—The Centre for Cardiovascular Biology and Medicine, The Rayne Institute, King's College, St Thomas' Hospital, London, UK; originally retrieved on Oct. 16, 2017, accessed Aug. 28, 2023 (12 pages).
Takemoto, et al., "The reciprocal protective effects of magnesium and calcium in hyperkalemic cardioplegic solutions on ischemic myocardium", Basic Research in Cardiology, 87(6):559-569, 1992 (11 pages).
Tane, et al., "Ex Vivo Lung Perfusion: A Key Tool for Translational Science in the Lungs", Chest, 151(6):1220-1228, Jun. 2017 (9 pages).
Taylor, et al., "Registry of the International Society for Heart and Lung Transplantation: Twenty-sixth Official Adult Heart Transplant Report—2009", Journal Heart and Lung Transplantation, 28(10):1007-1022, Oct. 2009 (16 pages).
Tipton, et al., "The use of Langendorff preparation to study the bradycardia of training", Medicine and Science in Sports, 9(4):220-230, 1977 (11 pages).
Unitslab.com, Online Converter, Lidocaine, https://unitslab.com/node/178, retrieved Aug. 29, 2023 (3 pages).
White et al., "Abstract 735: Impact of Initial Acidic Reperfusion on the Functional Recovery of DCD Hearts During Ex Vivo Heart Perfusion", Journal of Heart and Lung Transplantation, 34(4 Supplemental):S269-S270, Apr. 2015 (2 pages).
White, et al., "Abstract 385: Impact of Initial Acidic Reperfusion on the Functional Recovery of DCD Hearts During Ex Vivo Heart Perfusion", Canadian Journal Cardiology, 30:S251-252, 2014 (2 pages).
White, et al., "Impact of Reperfusion Calcium and pH on the Resuscitation of Hearts Donated After Circulatory Death", Annals of Thoracic Surgery, 103:122-130, Jan. 2017 (9 pages).
Wild et al., "PEEP and CPAP", British Journal of Anaesthesia, 1(3):89-92, 2001 (4 pages).
Zhong, et al., "The management experience of long duration roller pump ventricular assist device," Chinese Journal of ECC, 9(3):134-137, Sep. 15, 2011 (4 pages)—English Abstract Only.
Definition of AQUEOUS from Cambridge Dictionary, https://dictionary.cambridge.org/us/dictionary/english/aqueous, accessed Sep. 14, 2023 (2 pages).
Definition of MEDIUM, Collins English Dictionary, https://www.collinsdictionary.com/us/dictionary/english/medium#:~:text=You%20use%20medium %20to%20describe, middling%20More%20Synonyms%20of%20medium, accessed Sep. 14, 2023 (2 pages).

Ao ELECTRODE DETAIL

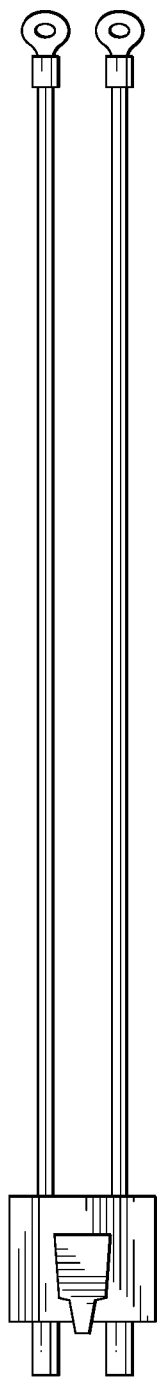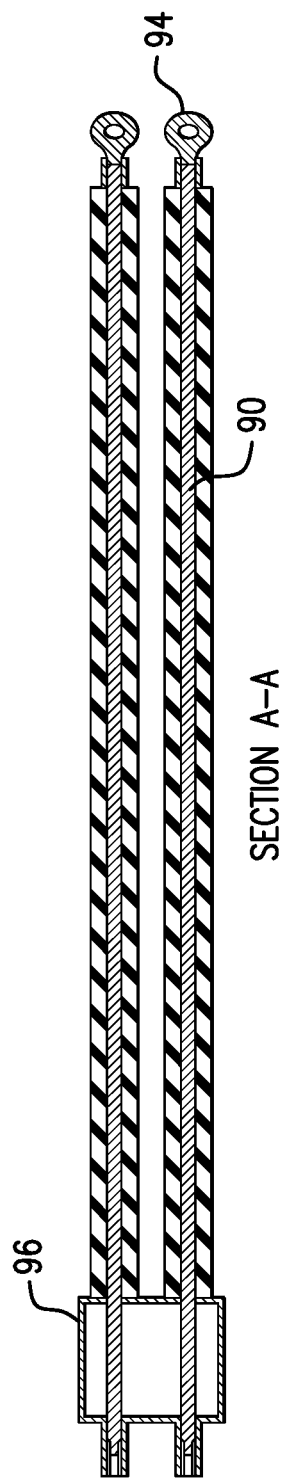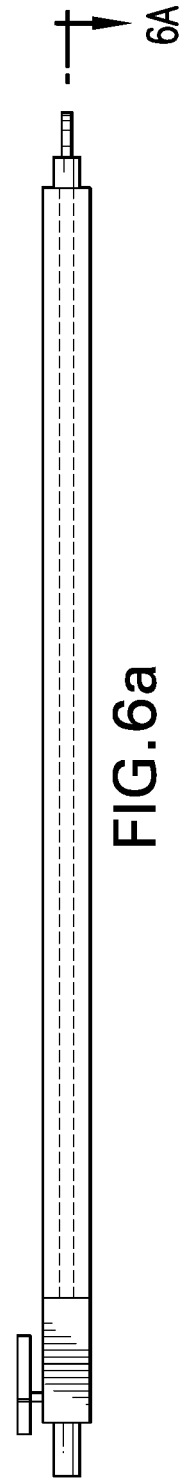

SYSTEMS FOR MONITORING AND APPLYING ELECTRICAL CURRENTS IN AN ORGAN PERFUSION SYSTEM

RELATED APPLICATIONS

This application is a divisional application of U.S. patent application Ser. No. 15/207,303, filed on Jul. 11, 2016; which is a continuation of U.S. patent application Ser. No. 11/822,495, filed on Jul. 6, 2007, which issued as U.S. Pat. No. 9,457,179 on Oct. 4, 2016; which claims the benefit of U.S. Provisional Patent Application No. 60/919,306, titled "Systems for Monitoring Organ Electrical Activity in a Perfusion System," filed on Mar. 20, 2007. The specifications of each of the foregoing are incorporated by reference in their entirety.

BACKGROUND OF THE INVENTION

Organ preservation techniques typically involve hypothermic storage of the organ in a chemical perfusate solution on ice. In the case of a heart, it is typically arrested, and cooled with a cardioplegic solution until it reaches a hypothermic, non-functioning state and then is stored in or perfused with a cold preservation solution. These techniques utilize a variety of cardioplegic and cold preservation solutions, none of which sufficiently protect the heart from myocardial damage resulting from ischemia. Such injuries are particularly undesirable when an organ, such as a heart, is intended to be transplanted from a donor into a recipient. In addition to myocardial damage resulting from ischemia, reperfusion of a heart may exacerbate the myocardial injury and may cause coronary vascular endothelial and smooth muscle injury, which may lead to coronary vasomotor dysfunction.

Using conventional approaches, such injuries increase as a function of the length of time an organ is maintained ex-vivo. For example, in the case of a heart, typically it may be maintained ex-vivo for only 4-6 hours before it becomes unusable for transplantation. This relatively brief time period limits the number of recipients who can be reached from a given donor site, thereby restricting the recipient pool for a harvested heart. Even within the 4-6 hour time limit, the heart may nevertheless be significantly damaged. A significant issue is that there may not be any apparent indication of the damage. Compounding the effects of cold ischemia, current cold preservation techniques preclude the ability to evaluate and assess an organ ex-vivo. Because of this, less-than-optimal organs may be transplanted, resulting in post-transplant organ dysfunction or other injuries. Thus, it would be desirable to develop techniques that can extend the time during which an organ can be preserved in a healthy state ex-vivo and that can provide an environment within which an organ can be evaluated ex-vivo. Such techniques would improve transplant outcomes and enlarge potential donor and recipient pools.

Effective maintenance of an ex-vivo organ would also provide numerous other benefits. For instance, ex-vivo maintenance of an organ in a living, functioning, near-physiologic state would permit more careful monitoring and evaluation of the harvested organ. This would in turn allow earlier detection and potential repair of defects in the harvested organ, further improving transplantation outcomes. The ability to perform simple repairs on the organ would also allow many organs with minor defects to be saved, whereas current transplantation techniques require them to be discarded.

In addition, more effective matching between the organ and a particular recipient may be achieved, further reducing the likelihood of eventual organ rejection. Current transplantation techniques rely mainly on matching donor and recipient blood types, which by itself is not a foolproof indicator of whether or not the organ will be rejected by the recipient. A more complete test for organ compatibility is a Human Leukocyte Antigen (HLA) matching test, but current cold ischemic organ preservation approaches preclude the use of this test, which can often require twelve hours or more to complete.

Prolonged and reliable ex-vivo organ care would also provide benefits outside the context of organ transplantation. For example, a patient's body, as a whole, can typically tolerate much lower levels of chemo-, bio- and radiation therapy than many particular organs. An ex-vivo organ care system would permit an organ to be removed from the body and treated in isolation, reducing the risk of damage to other parts of the body.

Electrodes are used in some heart perfusion systems to measure the electrical activity of the explanted heart and to deliver defibrillation energy. There are a number of issues associated with these electrodes, such as their size, which makes them difficult to position and may cause them to come in contact with each other resulting in erroneous signals, particularly on smaller hearts. In addition, these electrodes require wetting with blood to establish electrical contact with the heart, have a tendency to move around due to vibration during transport and beating of the heart resulting in a loss of signal fidelity, have biocompatibility issues, and are incompatible with the sterilization method (ETO) used to sterilize components of the perfusion systems.

SUMMARY OF EMBODIMENTS OF THE INVENTION

Electrode systems have been developed for use in perfusion systems to measure the electrical activity of an explanted heart and to provide defibrillation energy as necessary. The perfusion systems maintain the heart in a beating state at, or near, normal physiologic conditions; circulating oxygenated, nutrient enriched perfusion fluid to the heart at or near physiologic temperature, pressure and flow rate. These systems include a pair of electrodes that are placed epicardially on the right atrium and left ventricle of the explanted heart, as well as an electrode placed in the aortic blood path.

An advantage of this configuration allows an electrode to be held against the right atrium of the explanted heart under the heart's own weight, which reduces the likelihood that the electrode will shift during transport of the heart due to vibrations or the beating of the heart itself. As well, placing the electrode epicardially allows the electrode to be manipulated to ensure better electrical connection as well as adjustments for differently shaped and sized hearts.

Further, placement of an electrode in the aortic bloodpath supplies a more stable position for the sensing and detection of electrocardiogram (ECG) signals from the heart. This configuration provides an electrical connection for sensing and detecting ECG signals from the electrode in the aortic bloodpath, through the blood and heart muscle to the electrode, placed epicardially, on the right atrium. This electrode configuration has been shown to provide more stable ECG signals than two electrodes placed epicardially on the heart.

In addition to sensing and detecting ECG signals, the right atrial electrode, in combination with a left ventricle electrode, is used to deliver defibrillation energy and/or pacing signals to the explanted heart after being placed in a perfusion system to ensure the heart is beating normally before the organ chamber is sealed. After the heart is beating normally, the left ventricle electrode may be moved aside, such that fewer elements are in contact with the heart that may cause irritation to the tissue. However, it is envisioned that in some embodiments, the left ventricle electrode may be left in place after a normal heartbeat is achieved so defibrillation energy and/or pacing signals may be delivered to the heart after the organ chamber is sealed without the need for further manipulating the electrode through the membrane.

A perfusion system for maintaining an organ ex-vivo may include a housing comprising an outer lid and an intermediate lid. The intermediate lid covers an opening to the housing for substantially enclosing the organ within the housing, and includes a frame and a flexible membrane suspended within the frame. The flexible membrane includes sufficient excess membrane material to contact an organ contained within the chamber, which enables a medical operator to touch/examine the organ indirectly through the membrane or manipulate one or more electrodes contained within the organ chamber while still maintaining sterility of the system and the organ. The outer lid opens and closes over the intermediate lid independently from the intermediate lid. Preferably, the outer lid is rigid enough to protect the organ from physical contact, indirect or direct, and provide structural integrity to the organ chamber assembly.

The organ chamber assembly includes a pad or a sac assembly sized and shaped for interfitting within a bottom of the housing. Preferably, the pad assembly includes a pad formed from a material resilient enough to cushion the organ from mechanical vibrations and shocks during transport. In a preferred embodiment, the pad assembly is formed from silicone, which is biocompatible, impervious to liquids, capable of surviving sterilization processes (ETO, etc.) and provides a non-slip surface for electrodes. According to one embodiment, the pad of the invention includes a mechanism for receiving at least one electrode. The mechanism allows for adjustable placement of the at least one electrode on or in the pad to accommodate differently sized and shaped hearts. The pad may include a through-aperture through which an electrical lead of the at least one electrode may pass. The sac assembly may be two or more layers of silicone film sealed together and filled with air or fluid.

In all embodiments of the present invention, all blood and tissue contacting materials have been selected for their high degree of biocompatibility.

BRIEF DESCRIPTION OF THE DRAWINGS

FIGS. 6a-c illustrate an embodiment of a cable assembly for use with the electrodes of a system for delivering an electrical energy to an organ;

DETAILED DESCRIPTION OF THE INVENTION

Three electrodes are provided such that various connections may be made to a system for monitoring organ electrical activity in a perfusion system and providing, when appropriate, electrical energy to the organ. Two electrodes are placed proximate on an explanted heart, preferably within a sterile environment. A third electrode is placed in the flow of the aortic perfusion fluid. This configuration allows for the monitoring of ECG signals of the explanted heart as well as for the delivery of defibrillation energy and/or pacing signals to the heart.

Electrodes for epicardial placement are constructed of 304 stainless steel and are partially covered with silicone, which provides electrical insulation, is impervious to fluids, is biocompatible and provides a non-slip surface to aid in maintaining placement of the electrodes. The metal surface of the stainless steel electrodes is passivated to improve electrical performance, provide corrosion resistance and enhance biocompatibility. Electrodes for epicardial placement are resistance welded to 304 stainless steel wire contained within silicone insulation. The silicone wire insulation and silicone electrode covering are joined to provide protection for the weld as well as flexibility in the wire. The electrode placed in the flow of the aortic perfusion fluid is a thermal well constructed of 304 stainless steel and polycarbonate, into which has been potted a gold plated pin using electrically conductive epoxy. In certain embodiments, at least a portion of the electrode placed in the flow of the aortic perfusion fluid is covered with silicone to improved biocompatibility.

Placement of one electrode in the flow of the aortic perfusion fluid allows for more stable ECG readings as the electrode is less susceptible to vibrations during transport as well as movement from a beating heart. After a normal heartbeat is achieved, one electrode for epicardial placement may be removed or moved aside, which may reduce any potential irritation of the heart tissue, provide fewer opportunities for the electrodes to touch, as well as provide more maneuverability of the remaining electrode for obtaining better placement on the heart. After placement, the electrodes for epicardial placement are maintained in position, at least partially, by the weight of the explanted heart.

In operation, a completed electrical circuit for measuring ECG signals from the explanted heart exists from the electrode in the flow of the aortic perfusion fluid to an electrode for epicardial placement on the heart through the perfusion fluid and heart muscle. Defibrillation energy and/or pacing signals may be provided to the explanted heart by the electrodes.

EXAMPLES OF CERTAIN EMBODIMENTS

Figure 1:
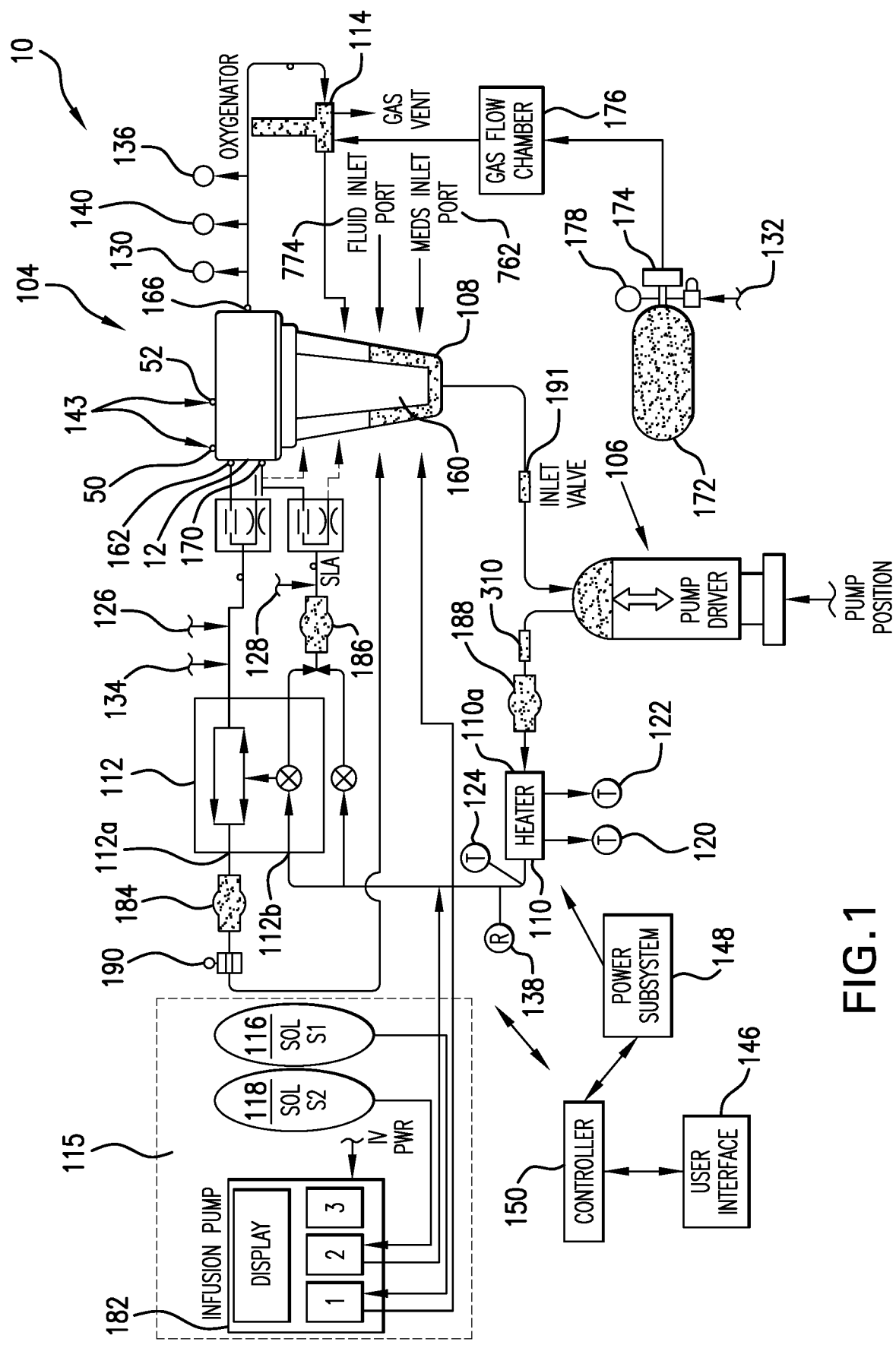
FIG. 1 illustrates a schematic diagram of a portable organ care system.

Illustrative apparatuses, systems and methods of perfusing an organ that may be adapted to incorporate the electrode systems of the present invention are described in U.S. application Ser. No. 11/246,902 titled "Systems and Methods for Ex-Vivo Organ Care," filed Oct. 7, 2005 now U.S. Pat. No. 8,465,970, which is incorporated herein by reference in its entirety, an example of which is shown in FIG. 1. Any operative combinations between any of the features, advantages, systems or methods described in any of the figures or applications upon which priority has been claimed or that have been incorporated by reference are considered part of the patentable subject matter contained herein.

Referring to FIG. 1, an embodiment of a perfusion system 10 is depicted, which includes an organ chamber assembly 104 for containing the heart 102 (not shown) during ex-vivo maintenance, a reservoir 160 for holding, defoaming and filtering the perfusion fluid 108, fluid inlet port 774 for loading perfusion fluid 108 into the reservoir 160 and a meds inlet port 762 for applying therapeutics to the fluid 108 contained in the reservoir 160, a perfusion fluid pump 106 for pumping/circulating perfusion fluid 108 to and from the harvested heart 102; a heater assembly 110 for maintaining the temperature of the perfusion fluid 108 at or near physiologic temperatures; a flow mode selector valve 112 for switching between normal and retrograde aortic flow modes (also referred to as "normal flow mode" and "retrograde flow mode," respectively); an oxygenator 114 for oxygenating the perfusion fluid 108 subsequent to it being deoxygenated by the heart 102 from aerobic respiration; a nutritional subsystem 115 containing an infusion pump 182 for replenishing energy substrates 116 in the perfusion fluid 108 as they are metabolized by the heart 102 and for providing additional nutrients and amino acids 118 to the perfusion fluid to reduce, for example, re-perfusion related injuries to the heart 102. An inlet valve 191 and the reservoir 160 are oriented to provide a gravity feed of perfusion fluid 108 into the pump assembly 106.

The illustrative perfusion system 10 also includes a plurality of sensors, including without limitation: temperature sensors 120, 122 and 124; pressure sensors 126, 128, 130 and 132; perfusion flow rate sensors 134, 136 and 138; a perfusion fluid oxygenation and hematocrit sensor 140; and sensor/defib electrodes 12, 50 and 52, and defibrillation source 143.

The system 10 further includes: various components employed for maintaining suitable flow conditions to and from the heart 102; an operator interface 146 for assisting an operator in monitoring operation of the system 10, and the condition of the heart 102, and for enabling the operator to select various operating parameters; a power subsystem 148 for providing fault tolerant power to the system 10; and a controller 150 for controlling operation of the organ care system 10.

With continued reference to FIG. 1, in both flow modes the perfusion fluid 108 flows from the pulmonary artery interface 166 into the oxygenator 114. The oxygenator 114 receives gas from an external or onboard source 172 through a gas regulator 174 and a gas flow chamber 176, which can be a pulse-width modulated solenoid valve that controls gas flow, or any other gas control device that allows for precise control of gas flow rate. A gas pressure gauge 178 provides a visual indication of amount remaining in the gas supply 172. The transducer 132 provides similar information to the controller 150. The controller 150 can regulate automatically the gas flow into the oxygenator 114 in dependence, for example, on the perfusion fluid oxygen content measured at the sensor 140. Subsequent to oxygenation, the oxygenator 114 returns the perfusion fluid 108 to the reservoir 160. In normal flow mode, the pulmonary vein interface 170 returns oxygenated blood to the left atrium of the heart 102. Blood leaves the left ventricle and enters the aorta interface 162. In retrograde flow mode, the aortic interface delivers oxygenated blood to the coronary arteries via the aorta. After the heart 102 is instrumented onto the system 100, the pump 106 is activated and the flow mode valve 112 is positioned in retrograde flow mode to pump the perfusion fluid 108 in retrograde flow mode through the aorta into the vasculature of the heart 102. The pumping of the warm, oxygen and nutrient enriched perfusion fluid 108 through the heart 102 allows the heart 102 to function ex vivo in a near normal physiologic state. In particular, the warm perfusion fluid 108 warms the heart 102 as it perfuses through it, which may cause the heart 102 to resume beating in its natural fashion.

As shown in FIG. 1, the system 10 also includes a plurality of compliance chambers 184, 186 and 188. The compliance chambers 184, 186 and 188 are essentially small inline fluid accumulators with flexible, resilient walls designed to simulate the human body's vascular compliance by aiding the system in more accurately mimicking blood flow in the human body, for example, by providing flow back-pressure and/or by filtering/reducing fluid pressure spikes due, for example, to flow rate changes and/or the pumping of the pump 106. The compliance chamber 184 is located between an output 112a of the mode valve 112 and the reservoir 160 and operates in combination with an adjustable clamp 190 during normal flow mode to provide back pressure to the aorta to cause perfusion fluid to flow into the coronary sinus to feed the heart 102. The compliance chamber 186 is located between an output 112b of the mode valve 112 and the pulmonary vein cannulation interface of the organ chamber assembly 104. The primary function of the compliance chamber 186 is to provide back-pressure to the left atrium and to smooth pressure/flow spikes caused from the pumping action of the perfusion fluid pump 106, which delivers blood to the heart without causing substantial fluid pressure spikes. The compliance chamber 188 is located between an output of a one-way valve 310 and an inlet 110a of the heater 110. The primary function of the compliance chamber 188 is also to smooth pressure/flow spikes caused by the pumping action of the perfusion fluid pump 106.

Figure 2:
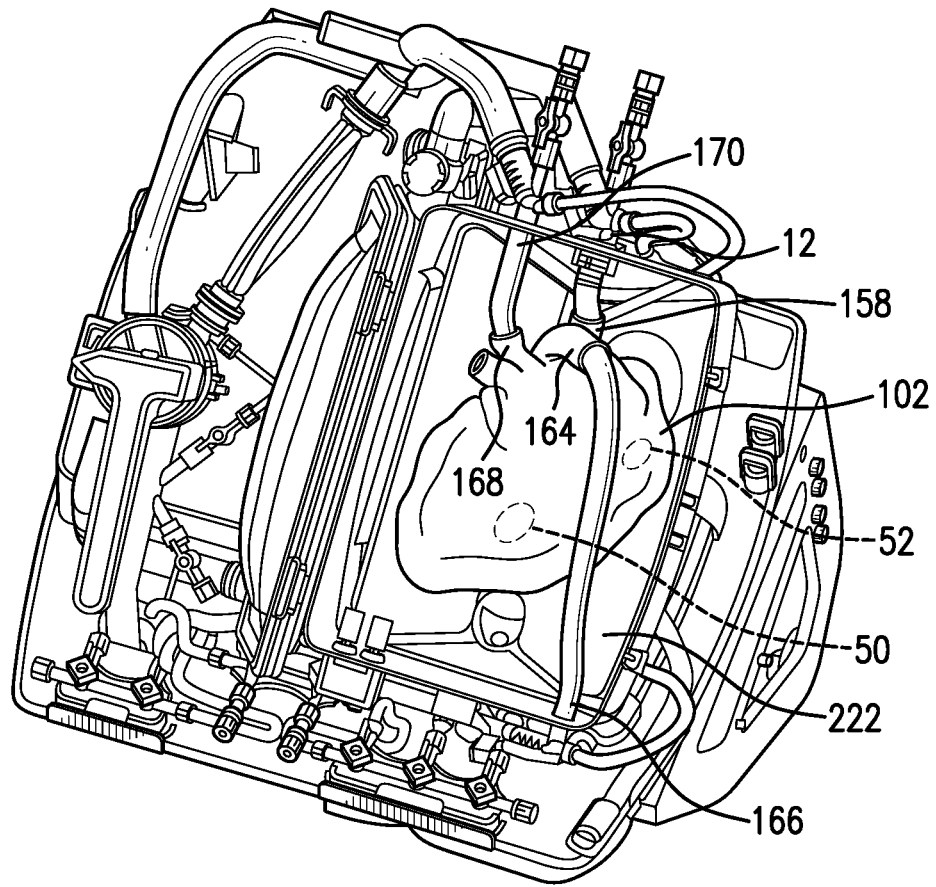
FIG. 2 illustrates an embodiment of an organ chamber assembly of the type employed in the organ care system of FIGS. 1 and 3.

FIG. 2 depicts an embodiment of an organ chamber assembly 104 of the type employed in the organ care system of FIG. 1. After explantation, an explanted heart 102 is perfused and transported to a donor site under sterile conditions while being monitored by a plurality of electrodes.

The heart rests and is supported by a foam pad or sac 222, preferably made of a biocompatible material resilient enough to cushion the heart 102 from vibrations and shocks during transport. In a preferred embodiment, the foam pad or sac 222 is comprised of silicone, although other biocompatible materials are envisioned. For reference, the heart is placed in a posterior arrangement, with the right atria in the top right and the left ventricle in the left-bottom. As shown, a right atrium electrode 52 and left ventricle electrode 50 are placed epicardially on the explanted heart 102 and are held in place by the weight of the heart 102 against the foam pad or sac 222. In a preferred embodiment, at least one side of at least one of the right atrial electrode 52 and left ventricle electrode 50 are over-molded with silicone, and friction created by the contact between the silicone over-molding of the at least one electrode and the silicone pad or sac 222 further aids in maintaining the epicardial placement of the electrode. The structure of the electrode is described in more detail below.

At least one of the right atrial electrode 52 and the left ventricle electrode 50 may be electrodes 142 and 144, described in U.S. application Ser. No. 11/246,902.

An aortic electrode 12 is placed in the aortic bloodpath for use in detecting ECG signals from the heart 102 during transport as blood travels to or from the aorta 158. The organ chamber assembly 104 includes apertures for the pulmonary artery interface 166, which carries perfusion fluid 108 from the pulmonary artery 164, and the pulmonary vein interface 170, which carries perfusion fluid to the pulmonary vein 168.

Figure 3:
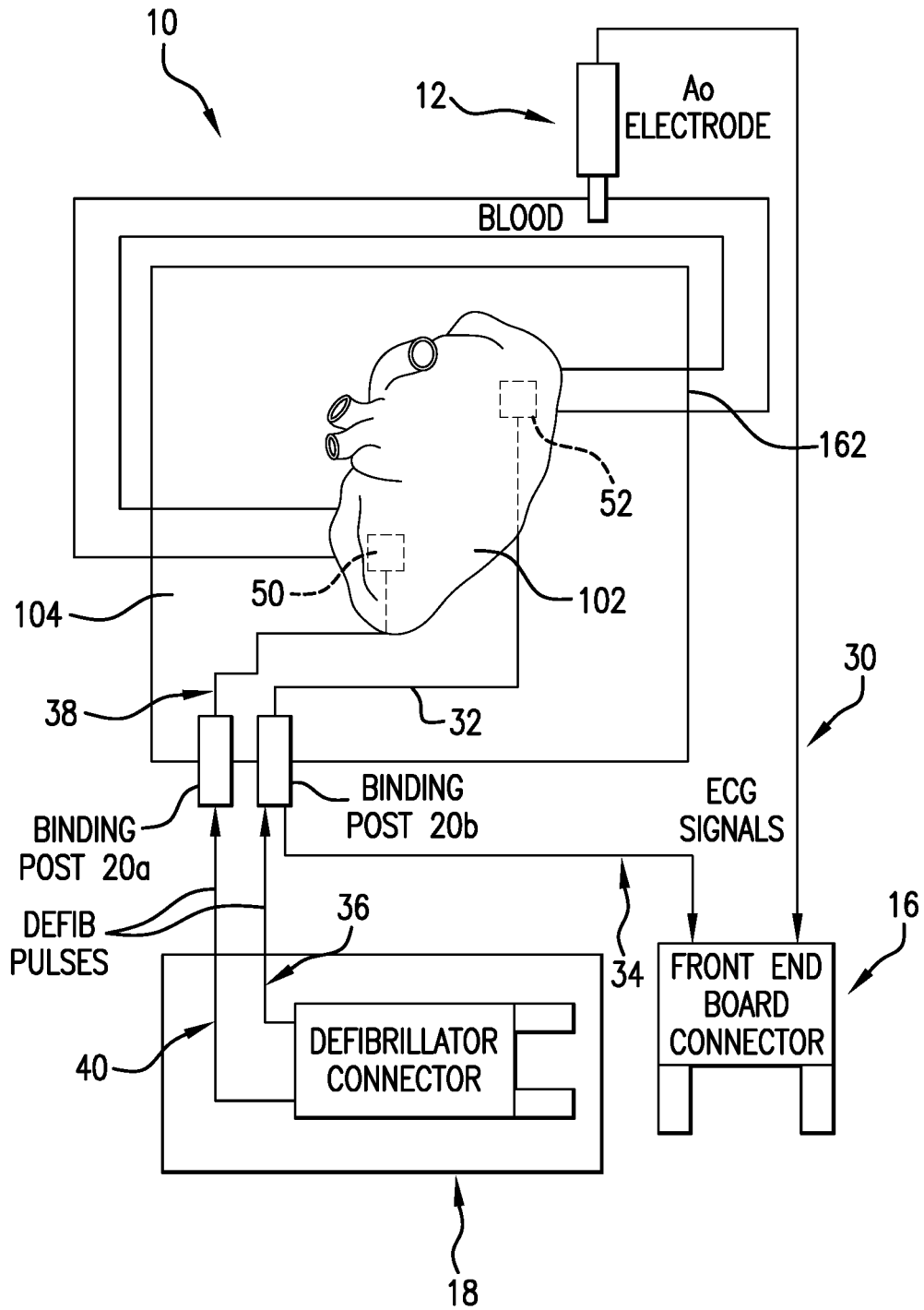
FIG. 3 illustrates an embodiment of an interconnection of the electrodes and signals flows of a system for monitoring organ electrical activity.

FIG. 3 depicts an interconnection of the electrodes and signal flows for monitoring organ electrical activity in a perfusion system 10. In a preferred embodiment, the system 10 allows monitoring of heart 102's electrical activity in a perfusion system as well as the delivery of defibrillation energy or pacing signals. The system 10 includes three electrodes: a right atrial electrode 52, a left ventricle electrode 50, and an aortic electrode 12.

The aortic electrode 12 is placed in the aortic blood path outside the organ chamber assembly 104, which provides a stable position from which ECG signals from the heart may be measured and is less susceptible to the electrode shifting due to movements from the beating heart or the vibrations in the system during transport. The right atrial electrode 52 and left ventricle electrode 50 are placed epicardially on the heart 102 within the organ chamber. Reference to "epicardially" includes, but is not limited to, on or near the heart. A silicone covering on at least a portion of the right atrial electrode 52 and the left ventricle electrode 50 aids in providing a non-slip surface to maintain the position of the electrodes.

According to one feature of the embodiment, the perfusion-fluid contacting components may be coated or bonded with heparin or other anticoagulant or biocompatible material to reduce the inflammatory response that may otherwise arise when the perfusion fluid contacts the surfaces of the components.

In a preferred operation, ECG signals are detected by both the aortic electrode 12 and the right atrial electrode 52. An electric circuit is completed between the aortic electrode 12, through the blood and heart muscle, to the right atrial electrode 52. This placement allows more variability in the placement of the right atrial electrode 52 within the organ chamber assembly 104 to accommodate differently shaped and sized hearts while maintaining a completed circuit.

In addition, using two epicardially placed electrodes within the organ chamber assembly 104 to detect ECG signals from the heart 102 increases the likelihood that the electrodes would touch due to being placed in an improper position or from shifting during transport, a possibility which is eliminated by the preferred configuration. In a preferred embodiment, the right atrial electrode 52 is at least partially held in place by the weight of the heart 102, which further aids in maintaining a completed circuit for detecting ECG signals.

Electrical connection is made by placing the heart 102 on the one or more electrodes. One advantage of the invention is that it does not require the electrodes to be permanently or temporarily sutured or otherwise mechanically connected to the heart 102. However, one skilled in the art would recognize circumstances in which such a connection is desirable. The present invention can be equally useful in such circumstances.

In certain embodiments, one or more electrodes are provided for placement in the bloodpath and one or more electrodes are provided for epicardial placement on an explanted heart. In these embodiments, ECG signals may be received by varying circuits comprising two electrodes placed in the bloodstream, two electrodes placed epicardially on the explanted heart, one electrode in the bloodstream and one electrode placed epicardially on the explanted heart, or any combination of the above. One of ordinary skill in the art will recognize that two electrodes are required to measure ECG signals, and as such, numerable combinations of electrode placements will provide ECG measurements.

After explantation, defibrillation energy and/or pacing signals may be necessary to restore a normal heartbeat during transport to a donor site. In addition to detecting ECG signals from the heart 102, the right atrial electrode 52, in conjunction with a left ventricle electrode 50, may be used to provide defibrillation energy and/or pacing signals to the explanted heart 102. In operation, after a normal heart rhythm is achieved by delivering a defibrillation energy and/or pacing signals to the heart 102, the left ventricle electrode 50 may be removed from the heart 102 by manipulating the electrode through the flexible membrane. Removing the electrode reduces the likelihood of irritation to the heart tissue during transport. However, it is envisioned in certain embodiments, that an operator may allow the left ventricle electrode 50 to remain epicardially placed should further defibrillation energy and/or pacing signals be required and without further need of manipulating the heart 102 and or electrodes 50 and 52.

A front-end board connector 16 is provided as an interface between at least one electrode and one or more subsystems of the system 10. At least one binding post 20, is provided to allow electrical connections to at least one electrode within the organ chamber assembly 104 while maintaining the sterile integrity of the chamber. The aortic electrode 12 is connected to the front-end board connector 16 by a first wire 30. The right atrial electrode 52 is connected to a binding post 20b by a second wire 32, which is connected to the front-end board connector by a third wire 34. This connection configuration allows a completed circuit for the measurement of ECG signals from the explanted heart 102. One of ordinary skill in the art will recognize that various other connections utilizing either fewer electrodes, wires or both could be used to achieve the same electrical circuit.

A defibrillator connector 18 is provided as an interface between at least one electrode and a defibrillation source for providing defibrillation energy and/or pacing signals to the heart 102. The right atrial electrode 52 is connected to a binding post 20b by a second wire 32, which is connected to the defibrillator connector 18 by a fourth wire 36. The left ventricle electrode 50 is connected to a binding post 20a by a fifth wire 38, which is connected to the defibrillator connector 18 by a sixth wire 40. This connection configuration allows a completed circuit for the delivery of defibrillation energy and/or pacing signals to the explanted heart 102. One of ordinary skill in the art will recognize that various other connections utilizing either fewer electrodes, wires or both could be used to achieve the same electrical circuit.

In a preferred embodiment, at least one of the first wire 30, third wire 34, fourth wire 36, and sixth wire 40 is a custom-made wire preferably comprised of tinned soft copped with a PVC jacket. At least one of the third wire 34, fourth wire 36, fifth wire 38, and sixth wire 40 is modified for purposes of defibrillation.

Figure 4A:
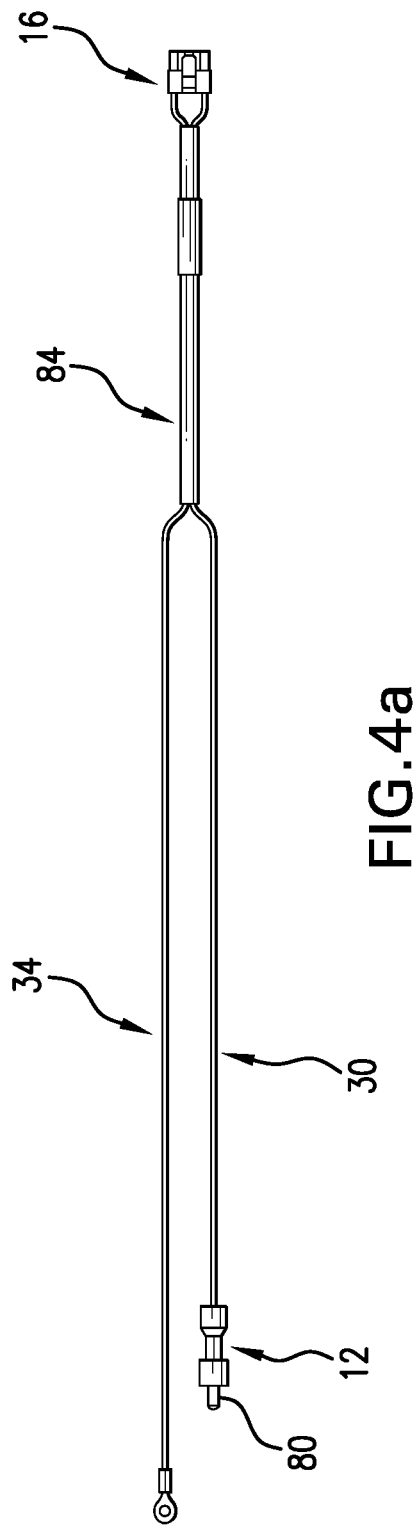
FIG. 4a illustrates an embodiment of an aortic electrode and interconnections for an interface to a system for monitoring organ electrical activity.
Figure 4B:
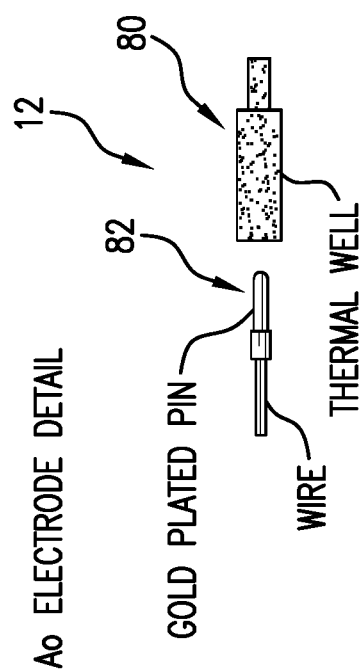
FIG. 4b illustrates an exploded view of an embodiment of an aortic electrode.

FIGS. 4a and 4b depict an embodiment of an aortic electrode and various interconnections that may be used to connect to the system.

As best seen in FIG. 4b, an aortic electrode 12 is comprised of a thermal well 80 comprised of 304 stainless steel and polycarbonate, into which a gold-plated pin 82 has been potted using electrically conductive epoxy. In a preferred embodiment, the epoxy must cure for two hours at 65° C. to fully cure. In other embodiments, it is envisioned that the aortic electrode may be comprised of other electrically conductive and biocompatible materials.

Referring to FIG. 4a, the aortic electrode is connected to a first wire 30. In a preferred embodiment, the first wire 30 and a third wire 34 are twisted together for approximately six inches and are covered in a heat shrink jacket 84.

Figure 5A:
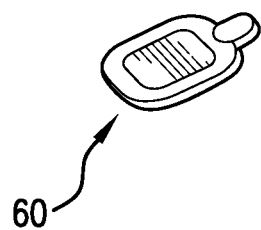
FIG. 5a illustrates an embodiment of an electrode for epicardial placement.
Figure 5B:
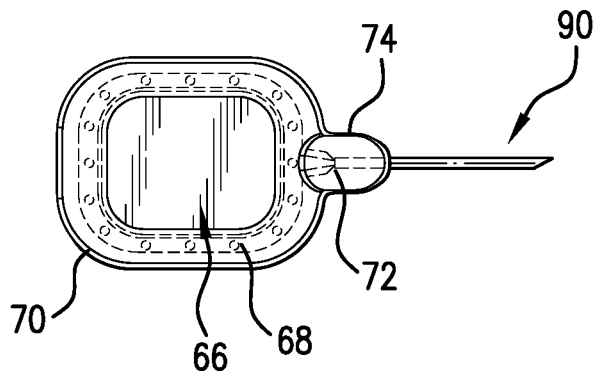
FIG. 5b illustrates a first side of an electrode for epicardial placement.
Figure 5C:
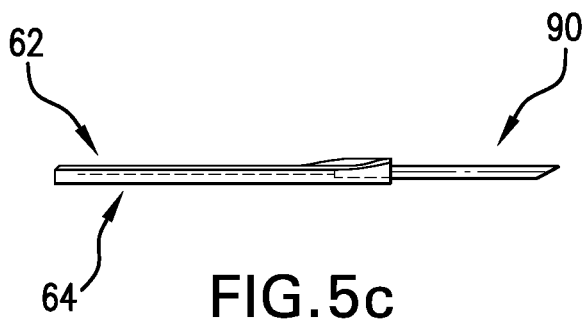
FIG. 5c illustrates a perspective view of an electrode for epicardial placement.

FIGS. 5a-c illustrate one embodiment of an electrode 60 for epicardial placement.

In a preferred embodiment, the epicardial electrodes are comprised of 304 stainless steel and over-molded with silicone. At least one aperture 68 in the stainless steel is provided to aid in securing the silicone to the stainless steel. The metal surface of the stainless steel is passivated to increase electrical performance, provide corrosion resistance and improve biocompatibility. Reference to "over-molded" includes, but is not limited to, covering or partially covering the electrode by means of molding, or other process that results in an electrode at least partially surrounded with silicone. Each epicardial electrode is resistance welded to 304 stainless steel wire 90 at a weld point 72, which is surrounded with silicone and which is terminated in a gold-plated pin. In a preferred embodiment, the over-molding of the wire 90 and the electrode 60 is overlapped at an interface 74 to reduce stress on the wire at the welding point but maintain wire flexibility.

The electrode 60 is approximately a one inch by one inch square (2.5 cm by 2.5 cm), with a rounded edge 70 to reduce irritation to the tissue. It is large enough to easily contact at least part of the critical heart area and small enough to not have two electrodes touch, particularly on a small heart. These dimensions allow the electrodes to be placed precisely as well as maintain sufficient current density, e.g., keep it below damage threshold, although other electrode sizes and shapes are contemplated. In alternative embodiments, it is envisioned that each of the epicardial electrodes and wire may be comprised of other electrically conductive materials and biocompatible materials.

Referring to FIGS. 5b and 5c, in a preferred embodiment, the electrode 60 is provided with a first side 62 and a second side 64. In one configuration, a portion 66 of the first side of the electrode 60 is exposed such that an electrical connection may be made epicardially with the heart 102 by placing the heart 102 on the first side 62. The second side 64 of the electrode 60 is over-molded with silicone such that it is electrically insulated. In a preferred embodiment, the silicone is General Electric LIM 6050 silicone with 50 Shore A hardness, or other similar silicones from Wacker, Bayer or Dow Corning. 304 stainless steel and silicone are chosen for their biocompatibility as well as resistance to fluids. Further, the materials chosen are also sufficiently resistant to the sterilization process (ETO) and to vacuum. Specifically, other materials (e.g., non-porous foams) used for electrode pads have experienced bending and deformation during an ETO sterilization process or biocompatibility issues (e.g., silver-silver chloride).

The silicone over-molding of the electrode 60 provides a non-slip surface when the electrode is placed against the pad or sac 222, which may also be constructed of silicone or have a surface that allows a reduced likelihood of slipping, which preferably aids in maintaining the positioning of the electrode after it has been epicardially placed on the heart 102.

Referring to FIG. 6a-c, a schematic view of the fourth wire 36 and sixth wire 40 is depicted. In an alternative embodiment, the wires are comprised of tinned soft copper wire 90 with PVC insulation or heat shrink tubing 92. Ring connectors 94 are provided to allow multiple connectors to the cabling. A connector 96 is provided for interconnection with the system 10. In a preferred embodiment, the connector 96 is the defibrillator connector 18. In a preferred embodiment, the cabling is modified for delivering defibrillation energy and/or pacing signals.

Figure 7:
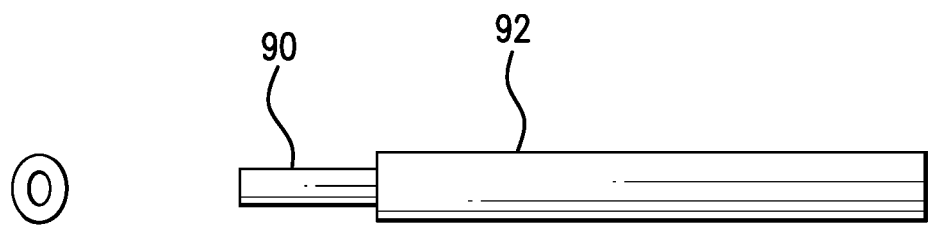
FIG. 7 illustrates an embodiment of a specially designed wire for use with the electrodes of a system for monitoring organ electrical activity.

Referring to FIG. 7, a schematic view of an embodiment of at least one of the second wire 32 and the fifth wire 38 is shown. In one embodiment, at least one of the second wire 32 and fifth wire 38 is 304 stainless steel wire 90 over-molded with silicone insulation 92. In a preferred embodiment, at least one of the second wire 32 and the fifth wire 38 is twenty gauge, multi-stranded soft-type 304 stainless steel and is over-molded with a 0.2 mm thick layer of silicone insulation.

Figure 8:
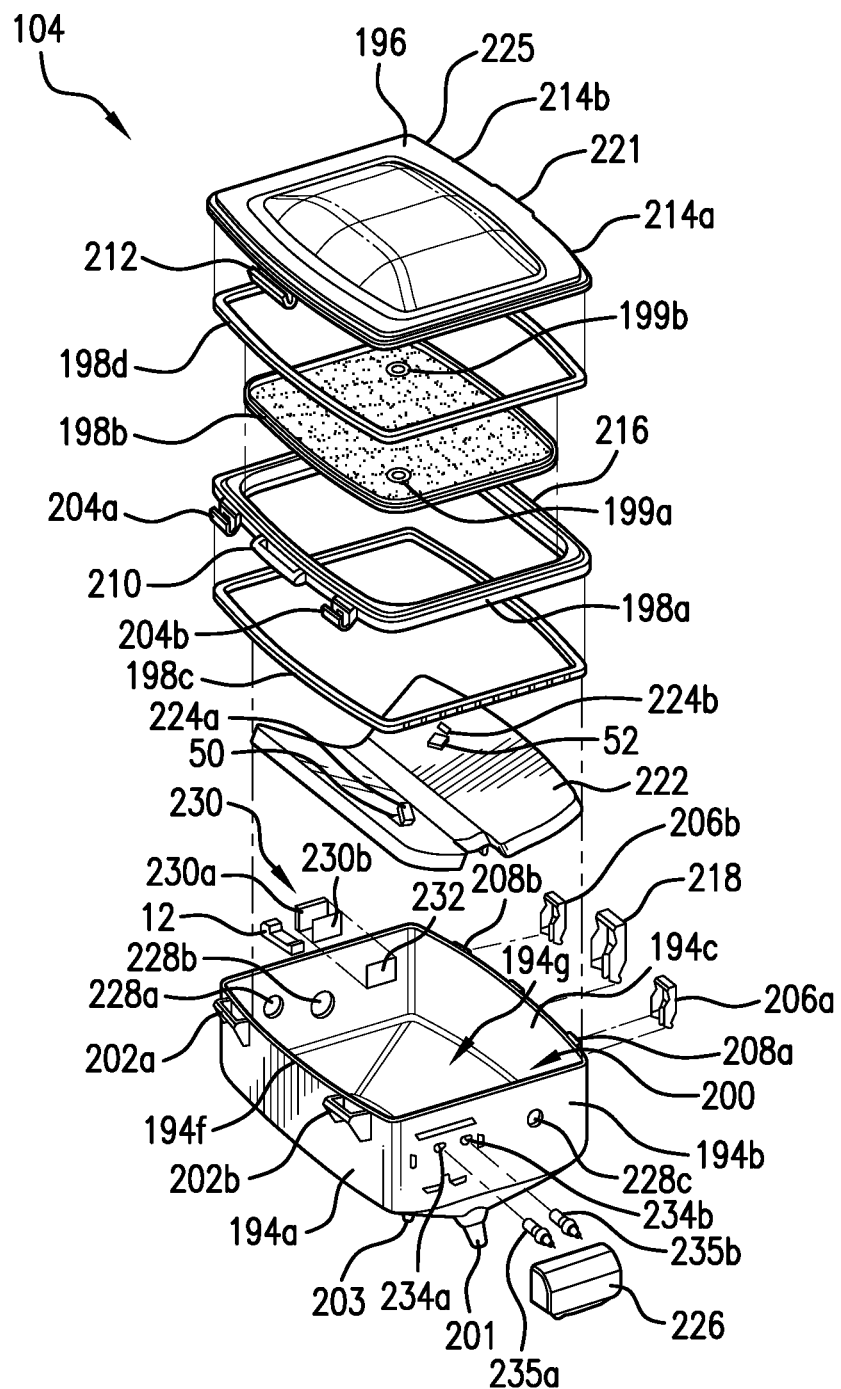
FIG. 8 illustrates an exploded view of an organ chamber assembly for use in a system for monitoring organ electrical activity.

FIG. 8 depicts an exploded view of the illustrative organ chamber assembly 104 of FIGS. 1, 2 and 3. The organ chamber assembly 104 includes a housing 194, an outer lid 196 and an intermediate lid 198. The housing includes a bottom 194g and one or more walls 194a-194d for containing the heart 102. The intermediate lid 198 covers an opening 200 to the housing 194 for substantially enclosing the heart 102 (not shown) within the housing 194. The intermediate lid 198 includes a frame 198a and a flexible membrane 198b suspended within the frame 198a. The flexible membrane 198b, preferably, is transparent but may be opaque, translucent, or substantially transparent.

According to one feature, the flexible membrane includes sufficient excess membrane material to contact the heart 102 when contained within the housing 194. This feature enables a medical operator to touch/examine the heart 102 indirectly through the membrane 198b, or apply an ultrasound probe to the heart 102 through the membrane 198b, while maintaining sterility of the housing 194. The membrane 198b may be made, for example, from any suitable flexible polymer plastic, for example polyurethane. Apertures 199a and 199b in the membrane 198b are provided through which electrodes 50 and 52 may be fed.

The outer lid 196 opens and closes over the intermediate lid 198 independently from the intermediate lid 198. Preferably, the outer lid 196 is rigid enough to protect the heart 102 from physical contact, direct or indirect. The outer lid 196 and the housing 194 may also be made from any suitable polymer plastic, for example polycarbonate.

According to one implementation, the housing 194 includes two hinge sections 202a and 202b, and the intermediate lid frame 198a includes two corresponding mating hinge sections 204a and 204b, respectively. The hinge sections 202a and 202b on the housing 194 interfit with the hinge sections 204a and 204b on the intermediate lid frame 198a to enable the intermediate lid 198 to open and close relative to the opening of the housing 194. The organ chamber assembly 104 also includes two latches 206a and 206b for securing the intermediate lid 198 closed over the opening 200. The latches 206a and 206b rotatably snap fit onto latch hinge section 208a and 208b, respectively, of the housing 194.

The intermediate lid frame 198a also includes a hinge section 210. The hinge section 210 rotatably snap fits with a mating hinge section 212 on the outer lid 196 to enable the outer lid 196 to open without opening the intermediate lid 198. The outer lid 196 also includes two cutouts 214a and 214b for enabling the latches 206a and 206b to clamp down on the edge 216 of the intermediate lid frame 198a.

The organ chamber assembly 104 also includes a latch 218, which rotatably snap fits onto a hinge part (not shown) on the wall 194c of the housing 194. In operation, the latch 218 engages a tab 221 on the edge 225 of the outer lid 196 to secure the outer lid 196 closed over the intermediate lid 198. The intermediate lid also includes two gaskets 198c and 198d. The gasket 198d interfits between a periphery of the intermediate lid frame 198a and a periphery of the outer lid 196 to form a fluid seal between the intermediate lid 198 and the outer lid 196 when the outer lid 196 is closed. The gasket 198c interfits between an outer rim 194f of the housing 194 and the intermediate lid frame 198a to form a fluid seal between the intermediate lid 198 and the periphery 194f of the housing 194 when the intermediate lid 198 is closed, thereby providing a sterile environment for the heart once the organ care system is removed from the sterile operating room.

Optionally, the organ chamber assembly 104 includes a pad 222 or a sac assembly sized and shaped for interfitting over an inner bottom surface 194g of the housing 194. Preferably, the pad 222 is formed from a material resilient enough to cushion the heart 102 from mechanical vibrations and shocks during transport, for example a silicone foam.

Again referring to FIG. 8, according to an illustrative embodiment, the mechanism includes two through-apertures 224a and 224b for passing electrical leads from the underside of the pad 222 to corresponding electrodes on the heart-contacting surface of the pad. Passing the electrical leads through the pad 222 to the electrodes enables the electrodes to be adjustably positioned within the pad 222 to accommodate variously sized hearts. In other embodiments, the mechanism may include, without limitation, one or more differently oriented slots, indentations, protrusions, through apertures, partially through apertures, hooks, eyelets, adhesive patches, or the like. In certain embodiments, the pad 222 may be configured with one or more sleeve-like structures that allow an electrode to be inserted within the pad 222, thus providing a membrane-like surface of the pad 222 positioned between the electrode and the heart 102.

In some illustrative embodiments, the pad 222 is configured as a pad assembly, with the assembly including one or more electrodes, such as the electrodes 50 and 52, adjustably located in or on the pad 222. According to one advantage, the pad/electrode configuration of the invention facilitates contact between the electrodes and the heart 102 placed on the pad 222, without temporarily or permanently suturing or otherwise mechanically connecting the electrodes to the heart 102. The weight of the heart 102 (illustrated in FIG. 9) itself can also help stabilize the electrodes during transport.

As shown in FIG. 8, the organ chamber assembly 104 includes electrical interface connections 235a-235b, which mount into the apertures 234a-234b, respectively, in the wall 194b of the housing 194. A cover 226 is provided for protecting the electrical interface connections 235a-235b. In a preferred embodiment, the electrical interface connections 235a-235b are at least one of the binding posts 20a-b of FIG. 3.

The interface connections 235a and 235b and aortic electrode 12 couple electrical signals, such as ECG signals, from the electrodes out of the housing 194, for example, to a controller and/or an operator interface. According to one embodiment, the electrodes couple to the controller and/or the operator interface via the front-end board connector 16 (not shown). The interface connections 235a and 235b may also couple to a defibrillation source, which may be either provided by external instrumentation or through circuitry within the system 10, and which can send a defibrillation and/or pacing signal through electrodes to the heart 102. According to one embodiment, the interface connections 235a and 235b are coupled to a defibrillation source via the defibrillation connector 18.

Still referring to FIG. 8, the organ chamber assembly 104 includes a resealable membrane interface 230, which mounts in an interface aperture 232. The interface 230 includes a frame 230a and a resealable polymer membrane 230b mounted in the frame 230a. The membrane 230b may be made of silicone or any other suitable polymer. In operation, the interface 230 is used to provide pacing leads, when necessary, to the heart 102, without having to open the chamber lids 196 and 198. The membrane 230b seals around the pacing leads to maintain a closed environment around the heart 102. The membrane 230b also reseals in response to removing the pacing leads.

The organ chamber assembly 104 also includes a drain 201 for draining perfusion fluid 108 out of the housing 194 back into the reservoir 160. Further, at least one mounting receptacle 203 is provided for mounting the organ chamber assembly 104 onto further components of the system 10. As well, a plurality of apertures 228a-c located on the organ chamber assembly 104 are provided for cannulation to vascular tissue of the heart 102.

Figure 9:
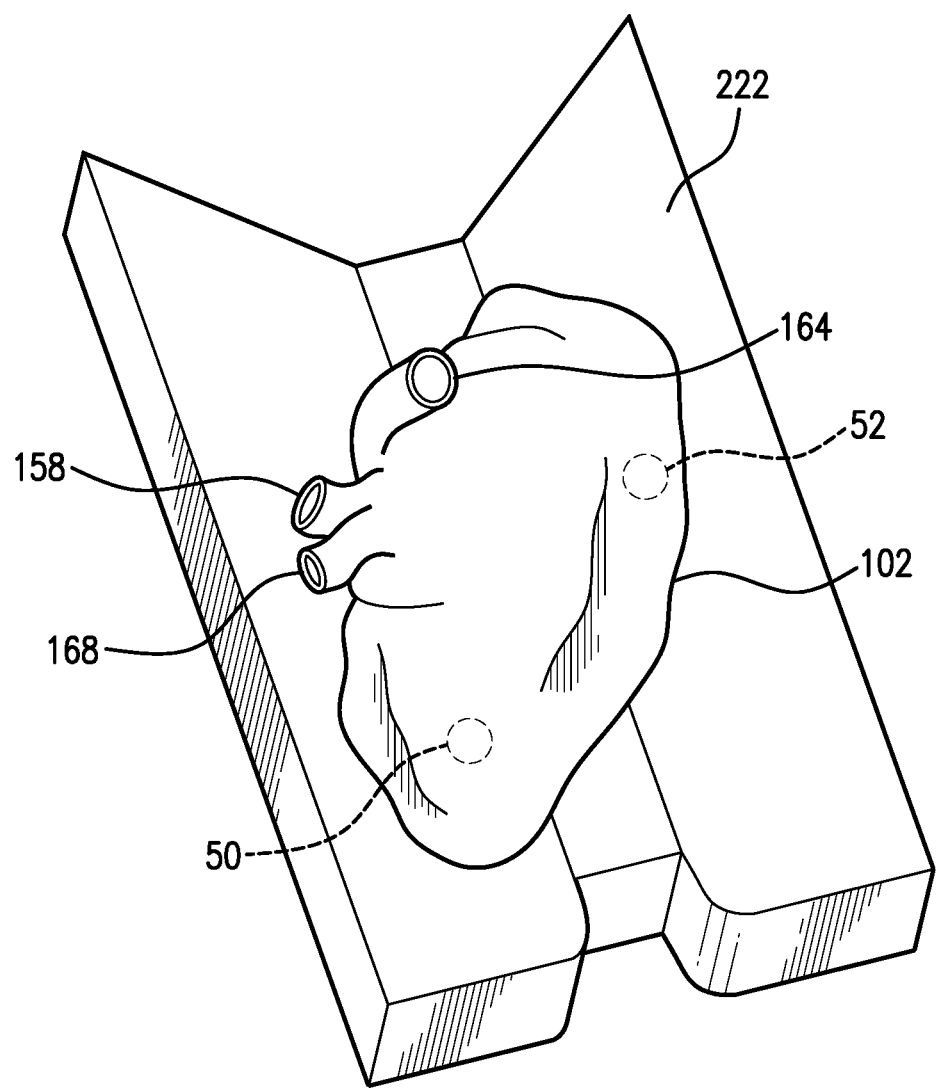
FIG. 9 illustrates the placement of an explanted heart on a pad containing electrodes for epicardial placement.

FIG. 9 depicts the placement of an explanted heart on a pad containing electrodes for epicardial placement. At least one of the right atrial electrode 52 and the left ventricle electrode 50 are at least partially held in place by the weight of the explanted heart 102 against the pad 222. As shown, the pulmonary artery 164, aorta 158, and pulmonary vein 168 are presented for cannulation.

Operationally, according to one embodiment, the heart 102 is harvested from a donor and cannulated into the organ chamber assembly 104. The perfusion fluid 108 is prepared for use within system 10 by being loaded into the reservoir 160 via fluid inlet port 774 and, optionally, being treated with therapeutics via meds inlet port 762. The pump 106 pumps the loaded perfusion fluid 108 from a reservoir 160 to the heater assembly 110. The heater assembly 110 heats the perfusion fluid 108 to or near a normal physiological temperature. According to another aspect, embodiments of the disclosed subject matter are directed to a method of preserving a heart ex vivo, the method including the steps of placing a heart on one or more electrodes in a protective chamber of a portable organ care system, pumping a perfusion fluid to the heart, the perfusion fluid being at a temperature of between about 25° C. and about 37° C., and at a volume of between about 200 ml/min and about 5 L/min, and monitoring electrical signals from the electrodes while pumping the perfusion fluid to the heart to preserve the heart ex vivo. According to one embodiment, the heater assembly 110 heats the perfusion fluid to between about 32° C. and about 37° C. The heater assembly 110 has an internal flow channel with a cross-sectional flow area that is approximately equal to the inside cross-sectional area of fluid conduits that carry the perfusion fluid 108 into and/or away from the heater assembly 110, so as to minimize disturbance of fluid flow. From the heater assembly 110, the perfusion fluid 108 flows to the flow mode selector valve 112.

One or more electrical signals related to the activity of the heart 102, e.g., ECG signals, are received by one or more electrodes 50 and 52 placed epicardially on the explanted heart 102. The one or more electrical signals are transmitted along at least one wire 32 and 38 inside the organ chamber to one or more binding posts 20a-b located at an interface between the inside of the organ chamber assembly 104 and the outside of the organ chamber. This binding post configuration allows one or more signals to enter and exit the organ chamber assembly 104 while maintaining the sterile environment within the organ chamber during transport of the explanted organ.

The binding posts 20a and 20b may send or receive one or more signals to one or more units, systems, controllers or the like for the maintenance of the heart 102. In one embodiment, one or more signals from electrodes 50 and 52 placed epicardially on an explanted heart 102 are transmitted to the binding posts 20a-b at the interface of the organ chamber assembly 104 and are received by a front-end board connector 16, which may be connected to one or more units, systems or controllers for measuring signals from the explanted heart 102 and providing responses to the one or more signals. In some embodiments, the one or more signals received by the front-end board connector 16 are used to determine at least one of, but not limited to, the rate of a pump for providing perfusion fluid to the explanted heart 102, the temperature to which the heating elements inside the heater should be set, determining whether pacing signals to maintain regular heart rhythm are required, the timing of pacing signals to be delivered to the heart 102, etc.

According to another advantage of the present invention, the binding posts 20a-b may send or receive at least one signal to a defibrillator connector 18. According to one embodiment, the defibrillator connector 18 sends signals to the binding posts 20a-b, which are received by electrodes placed epicardially on an explanted heart 102. It is contemplated that in some embodiments, the electrodes are a right atrial electrode 52 and a left ventricle electrode 50. In some embodiments, the signals sent by the defibrillator connector 18 are pacing signals for maintaining a proper heart rhythm of the explanted heart 102.

According to another embodiment of the present invention, signals received by the front-end board connector 16 are transduced and analyzed; the analysis determining at least one output signal from the defibrillator connector 18 to be transmitted to an explanted heart 102 by the binding posts 20a-b and electrodes placed on the explanted heart 102, respectively.

In the previous description, reference is made to the accompanying drawings that form a part of the present disclosure, and in which are shown, by way of illustration, specific embodiments of the invention. These embodiments are described in sufficient detail to enable those skilled in the art to practice the invention, and it is to be understood that other embodiments may be utilized and that structural and other changes may be made without departing from the scope of the present invention. The present disclosure is, therefore, not to be taken in a limiting sense. The present disclosure is neither a literal description of all embodiments of the invention nor a listing of features of the invention that must be present in all embodiments.

Numerous embodiments are described in this patent application, and are presented for illustrative purposes only. The described embodiments are not intended to be limiting in any sense. The invention is widely applicable to numerous embodiments, as is readily apparent from the disclosure herein. Those skilled in the art will recognize that the present invention may be practiced with various modifications and alterations. Although particular features of the present invention may be described with reference to one or more particular embodiments or figures, it should be understood that such features are not limited to usage in the one or more particular embodiments or figures with reference to which they are described.

The enumerated listing of items does not imply that any or all of the items are mutually exclusive. The enumerated listing of items does not imply that any or all of the items are collectively exhaustive of anything, unless expressly specified otherwise. The enumerated listing of items does not imply that the items are ordered in any manner according to the order in which they are enumerated.

The terms "a", "an" and "the" mean "one or more", unless expressly specified otherwise.

Headings of sections provided in this patent application and the title of this patent application are for convenience only, and are not to be taken as limiting the disclosure in any way.

Other embodiments, extensions, and modifications of the ideas presented above are comprehended and within the reach of one skilled in the art upon reviewing the present disclosure. Accordingly, the scope of the present invention in its various aspects should not be limited by the examples and embodiments presented above. The individual aspects of the present invention, and the entirety of the invention should be regarded so as to allow for modifications and future developments within the scope of the present disclosure. The present invention is limited only by the claims that follow.

What is claimed is:

1. An organ care system for maintaining an explanted heart at near physiologic conditions using a perfusion fluid, the organ care system comprising:
   an organ chamber assembly configured to contain the explanted heart;
   a heater assembly configured to heat the perfusion fluid to a temperature between 26° C. and 37° C.;
   a first electrode placed in an aortic bloodstream conduit;
   a second electrode connected to the organ care system;
   a third electrode connected to the organ care system; and
   a controller configured to:
      receive a signal from at least one of the first electrode or the second electrode, and
      control the heater assembly.

2. The organ care system of claim 1, wherein at least one of the second electrode or the third electrode is in a sterile environment.

3. The organ care system of claim 1, wherein at least one of the second electrode or the third electrode comprises stainless steel and is over-molded with silicone.

4. The organ care system of claim 1, wherein at least one of the second electrode or the third electrode is configured to be about a one inch by one inch square with a rounded edge.

5. The organ care system of claim 1, wherein at least one of the second electrode or the third electrode has a first side and a second side, wherein the first side is configured to be placed epicardially on the explanted heart, and wherein the second side is over-molded with silicone.

6. The organ care system of claim 1, wherein the first electrode is configured to be placed in the aortic bloodstream conduit outside the organ chamber assembly.

7. The organ care system of claim 1, wherein the organ chamber assembly further comprises a pad configured to hold the explanted heart, and wherein at least one of the second electrode or the third electrode is configured to be held in place against the pad by the explanted heart.

8. The organ care system of claim 1, further comprising a circuit, wherein the circuit comprises the first electrode, the second electrode, and the third electrode.

9. The organ care system of claim 1, wherein the heater assembly is configured to heat the perfusion fluid to a temperature between about 32° C. and about 37° C.

10. The organ care system of claim 1, further comprising a defibrillation source.

11. The organ care system of claim 10, further comprising a defibrillator connector configured to provide a defibrillation energy from the defibrillation source to the explanted heart.

12. The organ care system of claim 11, further comprising a defibrillation circuit wherein the second electrode is connected to a first wire, wherein the first wire is connected to a binding post, wherein the binding post is connected to the defibrillator connector by a second wire.

13. The organ care system of claim 12, wherein at least one of the first wire or the second wire comprises copper, and wherein the at least one of the first wire or the second wire comprises a PVC insulation or a heat shrink tubing.

14. The organ care system of claim 12, wherein at least one of the first wire or the second wire comprises stainless steel and is over-molded with silicone.

15. The organ care system of claim 12, wherein the third electrode is connected to a third wire, wherein the third wire is connected to a second binding post, wherein the second binding post is connected to the defibrillator connector by a fourth wire.

16. The organ care system of claim 15, wherein at least one of the third wire or the fourth wire comprises copper, and wherein the at least one of the third wire or the fourth wire comprises a PVC insulation or a heat shrink tubing.

17. The organ care system of claim 15, wherein at least one of the third wire or the fourth wire comprises stainless steel and is over-molded with silicone.

18. The organ care system of claim 1, wherein the second electrode is configured to be placed epicardially on the explanted heart.

19. The organ care system of claim 1, wherein the third electrode is configured to be placed epicardially on the explanted heart.

20. The organ care system of claim 7, wherein the pad comprises a through-aperture, wherein the through-aperture is configured to pass an electrical lead to a corresponding electrode.

21. The organ care system of claim 1, further comprising at least one binding post connected to at least one of the second electrode or the third electrode, wherein the binding post allows an electrical connection to the at least one of the second electrode or the third electrode within the organ chamber assembly.

22. The organ care system of claim 1, further comprising a front end board connector configured to receive a signal from at least one of the first electrode, the second electrode, or the third electrode, wherein the front-end board connector is connected to the controller.

* * * * *